US005502245A

United States Patent [19]

Dassel et al.

[11] Patent Number: 5,502,245

[45] Date of Patent: Mar. 26, 1996

[54] METHODS OF MAKING INTERMEDIATE OXIDATION PRODUCTS BY CONTROLLING TRANSIENT CONVERSION IN AN ATOMIZED LIQUID

[75] Inventors: Mark W. Dassel, Indianola, Wash.; Eustathios Vassiliou, Newark, Del.

[73] Assignee: Twenty-First Century Research Corporation, Newark, Del.

[21] Appl. No.: 477,234

[22] Filed: Jun. 7, 1995

[51] Int. Cl.[6] .................... C07C 51/16

[52] U.S. Cl. .................... 562/413; 562/512.4; 562/528; 562/538; 562/543; 562/529; 568/357; 568/358; 568/570; 568/836

[58] Field of Search .................... 562/512.4, 528, 562/538, 543, 529, 413; 568/358, 357, 836, 570

[56] References Cited

U.S. PATENT DOCUMENTS

| | | | |
|---|---|---|---|
| 1,121,532 | 12/1914 | Newberry . | |
| 2,014,044 | 9/1935 | Haswell | 75/17 |
| 2,301,240 | 11/1942 | Baumann | 183/115 |
| 2,980,523 | 4/1961 | Dille et al. | 45/215 |
| 3,530,185 | 9/1970 | Pugi | 260/586 |
| 3,613,333 | 10/1971 | Gardenier | 55/89 |
| 3,677,696 | 7/1972 | Bryk et al. | 23/2 |
| 3,928,005 | 12/1975 | Laslo | 55/73 |
| 3,987,100 | 10/1976 | Barnette et al. | 260/586 |
| 4,039,304 | 8/1977 | Bechthold et al. | 55/10 |
| 4,065,527 | 12/1977 | Graber | 261/79 A |
| 4,308,037 | 12/1981 | Meissner et al. | 55/10 |
| 4,361,965 | 12/1982 | Goumondy et al. | 34/57 |
| 4,370,304 | 1/1983 | Hendriks et al. | 422/224 |
| 4,423,018 | 12/1983 | Lester, Jr. et al. | 423/243 |
| 5,061,453 | 10/1991 | Krippl et al. | 422/106 |
| 5,123,936 | 6/1992 | Stone et al. | 55/8 |
| 5,170,727 | 12/1992 | Nielsen | 110/346 |
| 5,221,800 | 6/1993 | Park et al. | 562/543 |
| 5,244,603 | 9/1993 | Davis | 261/87 |
| 5,270,019 | 12/1993 | Melton et al. | 422/234 |
| 5,312,567 | 5/1994 | Kozma et al. | 261/87 |
| 5,321,157 | 6/1994 | Kollar | 562/543 |
| 5,396,850 | 3/1995 | Conochie et al. | 110/346 |
| 5,399,750 | 3/1995 | Brun et al. | 562/553 |

*Primary Examiner*—José G. Dees
*Assistant Examiner*—Samuel Barts
*Attorney, Agent, or Firm*—E. Vassiliou

[57] ABSTRACT

Methods of making intermediate oxidation products by atomizing a first liquid containing a reactant into a gas containing an oxidant in a manner to form an intermediate oxidation product different than carbon monoxide and/or carbon dioxide. The oxidation is controlled by monitoring the transient conversion (conversion taking place in the time interval between the formation of the droplets and their coalescence into a mass of liquid) of first reactant to oxidation product just before the droplets coalesce into a mass of a second liquid.

33 Claims, 12 Drawing Sheets

METHODS OF MAKING INTERMEDIATE OXIDATION PRODUCTS BY CONTROLLING TRANSIENT CONVERSION IN AN ATOMIZED LIQUID

FIELD OF THE INVENTION

This invention relates to methods of making intermediate oxidation products, wherein a first reactant incorporated in an atomized liquid reacts with a gas containing an oxidant, under controlled conditions.

BACKGROUND OF THE INVENTION

Reactions where a first reactant, dissolved in a liquid, reacts with a second reactant contained in a gas under increased surface area conditions are known to the art. Such reactions are carried out in devices as scrubbers, burners, reaction vessels, and the like, for example.

Atomization of liquids into a gaseous atmosphere is one of the above mentioned techniques described in the art. The atomization techniques for conducting reactions, disclosed in the art so far, are rather crude and lack innovative features for controlling such reactions with respect to: desired reaction product if the reaction product is an intermediate, yield in reaction product, conversion and conversion rate, temperature profiles in the reaction zone, average droplet size or diameter, evaporation rates, and the like. Actually in most, if not all, cases, the reaction product is substantially the final product expected under the crude overall conditions of the reaction. For example, in the case of a burner, where a fuel is atomized into an atmosphere of an oxygen-containing gas (such as air for example), the final product of reaction is carbon dioxide, with desired minimization of carbon monoxide and nitrogen oxides as much as possible. In another example, a scrubber for removing acidic compounds from a gas may use an atomized liquid containing alkali or alkaline earth compounds which react with the acidic compounds in the gas to form the corresponding salts. In still another example, ammonia and phosphoric acid react under atomization conditions to form ammonium orthophosphate, which is a final reaction product.

On the other hand, reactions which are geared to produce intermediate products, especially in the case of oxidations, are not run under atomization conditions, since atomization promotes complete reactions to a final product. For example, oxidation of cyclohexane to adipic acid, or oxidation of p-xylene to terephthalic acid, have not been reported to be conducted under atomization conditions, and there is no incentive in the art to do so, since burning of cyclohexane to carbon dioxide has been expected to take place under such conditions. However, the inventors have discovered that in the presence of unexpected intricate critical controls and requirements of the instant invention, intermediate reaction or oxidation products, such as adipic acid, phthalic acid, isophthalic acid and terephthalic acid, for example, may be advantageously obtained under atomization conditions.

The following references, among others, describe processes conducted in intermixing liquid with gaseous materials, mostly under increased surface area conditions.

U.S. Pat. No. 5,399,750 (Brunet al.) discloses methods for preparing maleamic acid (aminomaleic acid) by reacting gaseous ammonia with molten maleic anhydride under reactant contact conditions of high surface area, for example reacting said gaseous $NH_3$ with a thin film of said molten maleic anhydride or with said molten maleic anhydride in a state of vigorous agitation.

U.S. Pat. No. 5,396,850 (Conochie et al.) discloses a method of destroying organic waste in a bath of molten metal and slag contained in a vessel. The method comprises injecting organic waste into the bath to form a primary reaction zone in which the organic waste is thermally cracked and the products of the thermal cracking which are not absorbed into the bath are released into the space above the surface of the bath. The method further comprises injecting an oxygen-containing gas toward the surface of the bath to form a secondary reaction zone in the space above the surface of the bath in which the oxidizable materials in the products from the primary reaction zone are completely oxidized and the heat released by such oxidation is transferred to the bath. In order to facilitate efficient heat transfer from the second reaction zone to the bath, the method further comprises injecting an inert or other suitable gas into the bath to cause molten metal and slag to be ejected upwardly from the bath into the secondary reaction zone.

U.S. Pat. No. 5,312,567 (Kozma et al.) discloses a complex mixing system with stages consisting of propeller mixers of high diameter ratio, where the blades are provided with flow modifying elements, whereby the energy proportions spent on dispersion of the amount of gas injected into the reactor, homogenization of the multi-phase mixtures, suspension of solid particles, etc. and the properties corresponding to the rheological properties of the gas-liquid mixtures and to the special requirements of the processes can be ensured even in extreme cases. Open channels opposite to the direction of rotation are on the blades of the dispersing stage of the propeller mixers fixed to a common shaft, where the channels are interconnected with gas inlet. The angle of incidence of a certain part of the blades of mixing stages used for homogenization and suspension is of opposite direction and the length is shorter and/or the angle of incidence is smaller than those of the other blades. Baffle bars are on the trailing end of the blades on a certain part of the propeller mixers used similarly for homogenization and suspension, and/or auxiliary blades at an angle of max. 20° to the blade wings are arranged above or below the trailing end of the blades.

U.S. Pat. No. 5,244,603 (Davis) discloses a gas-liquid mixing system which employs an impeller/draft tube assembly submerged in liquid. Hollow eductor tubes affixed to the impeller drive shaft are used to flow gas from an overhead gas space to the liquid in the vicinity of the assembly. The positioning and size of the eductor tubes are such as to maximize the desired gas-liquid mixing and reaction rate.

U.S. Pat. No. 5,270,019 (Melton et al.) discloses an elongated, generally vertically extending concurrent reactor vessel for the production of hypochlorous acid by the mixing and reaction of a liquid alkali metal hydroxide and a gaseous halogen, wherein an atomizer is mounted near the top of the reactor vessel to atomize the liquid alkali metal hydroxide into droplets in the vessel. The vessel has a spraying and reaction zone immediately beneath the atomizer and a drying zone beneath the spraying and reaction zone to produce a gaseous hypochlorous acid and a substantially dry solid salt by-product.

U.S. Pat. No. 5,170,727 (Nielsen) discloses a processes and apparatus in which supercritical fluids are used as viscosity reduction diluents for liquid fuels or waste materials which are then spray atomized into a combustion chamber. The addition of supercritical fluid to the liquid fuel and/or waste material allows viscous petroleum fractions and other liquids such as viscous waste materials that are too viscous to be atomized (or to be atomized well) to now be atomized by this invention by achieving viscosity reduction and allowing the fuel to produce a combustible spray and improved combustion efficiency. Moreover, the present invention also allows liquid fuels that have suitable viscosities to be better utilized as a fuel by achieving further viscosity reduction that improves atomization still further by reducing droplet size which enhances evaporation of the fuel from the droplets.

U.S. Pat. No. 5,123,936 (Stone et al.) discloses a process and apparatus for removing fine particulate matter and vapors from a process exhaust air stream, and particularly those emitted during post-production curing or post-treatment of foamed plastics, such as polyurethane foam, in which the exhaust air stream is passed through a transfer duct into which is introduced a water spray in the form of a mist of fine droplets in an amount which exceeds the saturation point; thereafter the exhaust air stream is introduced into a filter chamber having a cross-sectional area that is substantially greater than that of the transfer duct, and the exhaust air stream passes through at least one, and preferably a plurality of high surface area filters, whereby a portion of the water is removed from the exhaust air stream and collected in the filter chamber prior to the discharge of the exhaust air stream into the environment.

U.S. Pat. No. 5,061,453 (Krippl et al.) discloses an apparatus for continuously charging a liquid reactant with a gas. The gas is dispersed in the reactant through a hollow stirrer in a gassing tank. The quantity of gas introduced per unit time is kept constant.

U.S. Pat. No. 4,423,018 (Lester, Jr. et al.) discloses a process according to which a by-product stream from the production of adipic acid from cyclohexane, containing glutaric acid, succinic acid and adipic acid, is employed as a buffer in lime or limestone flue gas scrubbing for the removal of sulfur dioxide from combustion gases.

U.S. Pat. No. 4,370,304 (Hendriks et al.) discloses methods by which ammonium orthophosphate products are prepared by reacting ammonia and phosphoric acid together at high speed under vigorous mixing conditions by spraying the reactants through a two-phase, dual coaxial mixer/sprayer and separately controlling the supply and axial outflow rate of the phosphoric acid at 1 to 10 m/sec. and the outflow rate of ammonia at 200 to 1000 m/sec. (N.T.P.). Thorough mixing and a homogenous product is obtained by directing the outflow spray into a coaxial cylindrical reaction chamber of a specified size with respect to the diameter of the outermost duct of the sprayer/mixer. The product may be granulated on a moving bed of granules and adjusted in respect of the $NH_3$ to $H_3PO_4$ content by changing the concentration of the phosphoric acid and/or supplying additional ammonia to the granulation bed.

U.S. Pat. No. 4,361,965 (Goumondy et al.) discloses a device for atomizing a reaction mixture, said device enabling the reaction mixture to be atomized in a reactor with the aid of at least a first gas and an atomizing nozzle. This device further comprises a supply of a second hot gas at the top of the atomizing device, serving to dry the atomized mixture, a supply of a third gas and means for distributing this third gas comprising an annular space of adjustable width and adapted to distribute in the reactor said third gas in the form of a ring along the inner wall of the reactor, so as to avoid any contact between the reaction mixture and said wall. The invention is applicable to the atomization of a reaction mixture.

U.S. Pat. No. 4,308,037 (Meissner et al.) discloses methods according to which high temperature thermal exchange between molten liquid and a gas stream is effected by generating in a confined flow passageway a plurality of droplets of molten liquid and by passing a stream through the passageway in heat exchange relationship with the droplets. The droplets are recovered and adjusted to a predetermined temperature by means of thermal exchange with an external source for recycle. The process provides for removal of undesired solid, liquid or gaseous components.

U.S. Pat. No. 4,065,527 (Graber) discloses an apparatus and a method for handling a gas and a liquid in a manner to cause a specific interaction between them. The gas is placed into circulation to cause it to make a liquid circulate in a vortex fashion to present a liquid curtain. The gas is then passed through the liquid curtain by angled vanes to cause the interaction between the two fluids, such as the heating of the liquid, scrubbing of the gas, adding a chemical to the liquid and the like. The vanes are spaced apart and project inwardly from the inner periphery of an annular support so that the circulating liquid readily moves into the spaces between the vanes to create the liquid curtain. A number of embodiments of the invention are disclosed.

U.S. Pat. No. 4,039,304 (Bechthold et al.) discloses methods according to which waste gas is contacted with a solution of a salt from a pollutant of the gas. This solution is obtained from another stage of the process used for cleaning or purifying the gas. The resulting mixture of gas and solution is subjected to vaporization so as to obtain a dry gaseous substance constituted by the waste gas and the evaporated solvent for the salt. The gaseous substance thus formed contains crystals of the salt as well as the pollutant present in the original waste gas. The salt crystals and other solid particles are removed from the gaseous substance in the form of a dry solids mixture. The gaseous substance is subsequently mixed with an absorption fluid such as an ammonia solution in order to wash out and redissolve any salt crystals which may remain in the gaseous substance and in order to remove the pollutant present in the original waste gas from the gaseous substance. The pollutant and the redissolved salt crystals form a salt solution together with the absorption fluid and it is this salt solution which is brought into contact with the waste gas. The gaseous substance is exhausted to the atmosphere after being mixed with the absorption fluid.

U.S. Pat. No. 3,928,005 (Laslo) discloses a method and apparatus for treating gaseous pollutants such as sulfur dioxide in a gas stream which includes a wet scrubber wherein a compressed gas is used to atomize the scrubbing liquid and a nozzle and the compressed gas direct the atomized liquid countercurrent to the flow of gas to be cleaned. The method and apparatus includes pneumatically conveying to the nozzle a material such as a solid particulate material which reacts with or modifies the pollutant to be removed or altered. The gas used for atomizing the scrubbing liquid is also used as a transport vehicle for the solid particulate material. In the case of sulfur oxides, the material may be pulverized limestone.

U.S. Pat. No. 3,677,696 (Helsinki et al) discloses a method according to which, the concentration of circulating sulfuric acid is adjusted to 80–98% by weight and used to wash hot gases containing mercury. The temperature of the acid is maintained between 70°–250° C., and the solid material separating from the circulating wash solution is recovered.

U.S. Pat. No. 3,613,333 (Gardenier) discloses a process and apparatus for removing contaminants from and pumping a gas stream comprising indirectly heat exchanging the gas and a liquid, introducing the liquid under conditions of elevated temperature and pressure in vaporized and atomized form into the gas, mixing same thereby entrapping the contaminants, and separating clean gas from the atomized liquid containing the contaminants.

U.S. Pat. No. 2,980,523 (Dille et al.) discloses a process for the production of carbon monoxide and hydrogen from carbonaceous fuels by reaction with oxygen. In one of its more specific aspects it is directed to a method of separating carbonaceous solid entrained in the gaseous products of reaction of carbonaceous fuels and oxygen wherein said products are contacted with a limited amount of liquid hydrocarbon and thereafter scrubbed with water, and said carbonaceous solid is decanted from said clarified water.

U.S. Pat. No. 2,301,240 (Leuna et al.) discloses an improved process for removing impurities from acetylene gas which has been prepared by thermal or electrical methods by washing with organic liquids, as for example oils or tars.

U.S. Pat. No. 2,014,044 (Haswell) discloses an improved method for treating gas and aims to provide for the conservation of the sensible heat of such gas.

U.S. Pat. No. 1,121,532 (Newberry) discloses a processes of recovering alkalis from flue-gases.

Currently, oxidation reactions for the production of organic acids, including but not limited to adipic acid, are conducted in a liquid phase reactor with reactant gas sparging. The reactant gas in these cases is typically air, but may also be oxygen. Sufficient reactant gas, with or without non-reactive diluents (e.g., nitrogen), is sparged—at relatively high rate—so that the liquid reaction medium is aerated to maximum capacity (typically 15–25% aeration). The relatively high sparging rates of reactant containing gas feed (hereinafter referred to as "reactant gas"), associated with this conventional approach, have several drawbacks:

Costly reactant gas feed compressors are required to compress makeup reactant gas for sparging. These are expensive to install and operate (high electric or steam consumption), and have many utility problems resulting in excessive plant downtime.

The required high gas rate makes it extremely difficult to control oxygen content in the reactor at low concentrations (due to the high reactor gas turnover rate).

The required high gas rate makes it extremely difficult to control reaction temperature at low production rates (i.e., high turndown rate) for a given sized reactor system. This occurs because the gas used for sparging removes energy from the reaction system by volatilizing reaction liquid and liquid solvent—this volatilization effect is quite significant at the relatively high temperatures commonly associated with and required for oxidation reactions. Unless carefully balanced by an exothermic heat of reaction, this volatilization will act to substantially lower the temperature of the liquid content of the reactor. Thus, a properly sparged system can be designed for good temperature control at medium to high production rates, but will suffer temperature loss and loss of temperature control at significant turndown rate.

High reactant gas feed rate results in relatively high reactor non-condensible off-gas rate. Non-condensible off-gases must either be totally purged to atmosphere, or—if oxygen content is high—partially purged and partially recycled to the reactor. The use of air as a reactant gas feed has drawbacks because it results in high rate of purge to the atmosphere—this is undesirable because this purge must first be cleaned in very expensive off-gas cleanup facilities in order to meet ever more stringent environmental requirements. The use of oxygen-only gas feed to the reactor may be undesirable because high sparging requirements result in low oxygen conversion in the reactor; low conversion results in high oxygen concentration within the reactor; and high oxygen concentration within the reactor may result in excessive over-oxidation of liquid reactants and liquid solvents with attendant high chemical yield loss (i.e., burning these to carbon monoxide and carbon dioxide). If the oxygen in the reactor is diluted with recycle nitrogen or gaseous-recycle inerts, then both high recompression investment and costs, and recompression utility problems are introduced.

The current technology also suffers from a relatively low ratio of gas-liquid surface area to liquid reaction mass. The presently available art does not maximize this ratio. In contrast, the present invention maximizes said ratio in order:

to increase reaction rate by increasing the mass transfer rate of gaseous reactants (oxygen) to liquid reaction sites; and so as to enable economic operation at relatively low oxygen concentration in the gas phase.

Operating at lower oxygen concentration with acceptable conversion rates in the reactor improves yield by reducing over-oxidations, and eliminates safety (explosion) problems associated with operation in the explosive oxygen/fuel envelope. In the current technology, reducing oxygen content below traditional levels would result in a non-economic reduction in reaction rate. However, a significant increase in the aforementioned ratio—relative to current levels—would offset this rate reduction thereby enabling economic operation at reduced oxygen concentration in the reactor.

Another problem with the current technology is the sometimes formation of large agglomerations of insoluble oxidation products in the reactor. These can build up on reactor walls resulting in decreased available reaction volume, and in unwanted by-product formation due to over-exposure of said accretions to reaction conditions (e.g., high temperature) in oxygen-starved micro-reactor environments. These can also form large diameter, heavy solids in the reactor which can result in damage to expensive reactor agitator shafts and agitator seals resulting in costly repairs and high utility wear-problems. Finally, the current technology often requires expensive agitation shafts and seals capable of withstanding corrosive chemical attack and containing high system pressures.

Substituting gas-phase reaction systems for liquid-phase reactors introduces new problems, chief among which is the difficulty of identifying a cost-effective, efficient, non-plugging, long-lived catalyst system. Liquid-phase catalyst systems are well-developed and well-understood. Unfortunately, these are non-volatile. Using a non-volatile catalyst in a gas-phase reaction system must necessarily often be subject to severe plugging problems as most organic acids resulting from oxidation reactions are non-volatile solids—unless dissolved in a liquid reaction medium.

There is a plethora of references dealing with oxidation of organic compounds to produce acids, such as, for example, adipic acid.

The following references, among the plethora of others, may be considered as representative of oxidation processes relative to the preparation of diacids.

U.S. Pat. No. 5,321,157 (Kollar) discloses a process for the preparation of $C_5$–$C_8$ aliphatic dibasic acids through oxidation of corresponding saturated cycloaliphatic hydrocarbons by (1) reacting, at a cycloaliphatic hydrocarbon conversion level of between about 7% and about 30%,
(a) at least one saturated cycloaliphatic hydrocarbon having from 5 to 8 ring carbon atoms in the liquid phase and
(b) an excess of oxygen gas or an oxygen containing gas mixture in the presence of
(c) less than 1.5% moles of a solvent per mole of cycloaliphatic hydrocarbon (a), wherein said solvent comprises an organic acid containing only primary and/or secondary hydrogen atoms and
(d) at least about 0.002 mole per 1000 grams of reaction mixture of a poly valent heavy metal catalyst; and
(2) isolating the $C_5$–$C_8$ aliphatic dibasic acid.

U.S. Pat. No. 5,221,800 (Park et al.) discloses a process for the manufacture of adipic acid, according to which cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to 150° C., at an oxygen partial pressure of about 50 to about 420 pounds per square inch absolute.

The following references, among others, describe oxidation processes conducted in multi-stage and multi-plate systems.

U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,530,185 (Pugi) describes a process for manufacturing precursors of adipic acid by oxidation of an oxygen containing inert gas which process is conducted in at least three successive oxidation stages by passing a stream of liquid cyclohexane maintained at a temperature in the range of 140° to 200° C., and a pressure in the range of 50–350 psig through each successive oxidation stage in an amount such that substantially all the oxygen introduced into each stage is consumed in that stage thereafter causing the residual inert gases to pass countercurrent into the stream of liquid during the passage of the stream through said stages.

None of the above references, or any other references known to the inventors disclose, suggest or imply, singly or in combination, oxidation reactions to intermediate oxidation products under atomization conditions subject to the intricate and critical controls and requirements of the instant invention as described and claimed.

SUMMARY OF THE INVENTION

As aforementioned, the present invention relates to methods of making intermediate oxidation products, wherein a first reactant incorporated in an atomized liquid reacts with a gas containing an oxidant, under controlled conditions. More particularly, this invention pertains a method of preparing an intermediate oxidation product from a first liquid containing a first reactant and a gas containing an oxidant, the method comprising the steps of:

atomizing the first liquid to form a plurality of droplets in the gas at an atomization temperature and at an atomization distance from a mass of a second liquid;

causing a substantially non-destructive oxidation at an oxidation pressure between the first reactant and the oxidant to form the intermediate oxidation product;

coalescing the droplets into the mass of the second liquid;

controlling transient conversion of the first reactant and the oxidant to intermediate oxidation product in the droplets to be within a predetermined pre-coalescing transient conversion range, before said droplets coalesce into the second liquid; and separating the intermediate oxidation product from the second liquid.

Transient conversion is the conversion taking place in the time interval between the formation of the droplets and their coalescence into a mass of liquid. For more details see more detailed explanations at the last section of this specification.

Atomization temperature is the temperature of the first liquid in the atomizer, just before the first liquid has been atomized.

The methods and devices of the instant invention give vastly superior control over conventional methods and devices, since any reactions taking place within the droplets, substantially freeze (substantially stop) as the droplets coalesce. This, combined with measurements of miscellaneous characteristics of the droplets, just before they coalesce into the second liquid (where the reaction substantially freezes), gives key information on how to change different reaction parameters in order to control the reaction in an unprecedented manner.

According to this invention, a controller points the transient conversion in the droplets toward a predetermined conversion range. By this, it is meant that the controller is adapted to change one or more parameters or variables, such as the preferable variables listed as examples below, so that said change will favor a respective change in the transient conversion toward the predetermined range.

Depending on the reaction characteristics, some parameters or variables may be more or less effective and efficient in causing changes to the transient conversion. It is possible in some occasions that changes in one parameter may not be capable to bring the transient conversion within the predetermined range. In such cases, the controller is preferably adapted or programmed to select and change one or more additional variables in order to receive the desired result.

In the description of the preferred embodiments of the instant invention, it is assumed for purposes of clarity that the particular variable under consideration is capable by itself to bring the transient conversion within the predetermined range. This is generally true, provided that for a particular reaction, conducted in the devices and by the methods of this invention, the most efficient variable(s) has been selected to be controlled by the controller. It should be understood, however, that the selection of one or more additional variables is well within the scope of this invention.

The droplets have an average droplet diameter and are produced at a desired first flow rate, the gas flows at a second flow rate, the droplets contain volatile ingredients volatilizing at a volatilization rate, the first liquid contains first reactant at a first content, the gas contains oxidant at a second content, and the control of the transient conversion is performed by a step selected from a group consisting of changing the atomization temperature, changing the reaction pressure, changing the atomization distance, changing the average droplet diameter, changing the first flow rate, changing the second flow rate, changing the volatilization rate, changing the first content, changing the second content, and a combination thereof.

It is preferable that the transient conversion is monitored by a chromatographic method, and more preferably by High Performance Liquid Chromatography, especially in the case that the oxidation product(s) comprises an acid.

It is further preferable that a major portion of the oxidation product is an organic compound, and/or the first reactant is an organic compound, and/or the oxidant is oxygen, and/or the major portion of the oxidation product is an intermediate oxidation product different than CO, $CO_2$ or a mixture thereof, and/or the major portion of the intermediate oxidation product is an organic acid. By the expression "major portion" referring to a certain compound or compound group, it is meant that the weight of the compound or compound group is higher than the weight of any other individual by-product formed.

It is even more preferable that the intermediate oxidation product is adipic acid, or an acid selected from the group consisting of phthalic acid, isophthalic acid, and a mixture thereof.

The predetermined transient conversion range is preferably in the range of 5% to 80%, more preferably in the range of 10–70%, and even more preferably in the range of 20–60%.

It is also preferable that the first reactant comprises a compound selected from a group consisting of cyclohexane, cyclohexanone, cyclohexanol, cyclohexylhydroperoxide, o-xylene, p-xylene, m-xylene, a mixture of at least two of cyclohexane, cyclohexanone, cyclohexanol, and cyclohexylhydroperoxide, and a mixture of at least two of o-xylene, p-xylene, and m-xylene.

It is also preferable that the first reactant comprises a compound selected from a group consisting of cyclohexane, cyclohexanone, cyclohexylhydroxyperoxide, cyclohexanol, o-xylene, m-xylene, p-xylene, a mixture of at least two of cyclohexane, cyclohexanone, cyclohexanol, and cyclohexylhydroxyperoxide, and a mixture of at least two of o-xylene, p-xylene, and m-xylene.

the oxidant comprises oxygen; and a major portion of the reaction product comprises a compound selected from a group consisting of adipic acid, cyclohexanol, cyclohexanone, cyclohexylhydroperoxide, phthalic acid, isophthalic acid, terephthalic, a mixture of at least two of adipic acid, cyclohexanone, cyclohexanol, and cyclohexylhydroxyperoxide, and a mixture of at least two of phthalic acid, isophthalic acid, and terephthalic acid.

It is further preferable that the step of atomizing is performed by spraying the first liquid from a point over the second liquid at the atomization distance, and more preferable that spraying is performed by an airless technique.

At least part of the second liquid may be recirculated, and a third liquid containing first reactant may be also added to the first liquid to replenish first reactant consumed during the substantially non-destructive oxidation.

In the case that the intermediate oxidation product is a solid, it is preferred that the step of separating said intermediate oxidation product from the second liquid includes a step of filtering the intermediate oxidation product out of the second liquid.

In order to prevent development of electrostatic charges and sparking, an adequate amount of antistatic compound, preferably water, may be added to a component selected from a group consisting of the first liquid, the gas, and a combination thereof.

It is preferable that the condensibles are condensed internally, substantially under reaction pressure, and further it is also preferable that the non-destructive oxidation is conducted in a reaction zone surrounded by a thick film or curtain of liquid.

The methods of this invention may further comprise a step of adding a catalyst to the first liquid, the catalyst comprising metal ions, the ions being able to exist at a state selected from a group consisting of a lower valance state, a higher valance state, and a mixture thereof, the catalyst having been formed by steps of atomizing a solution comprising metal ions of the lower valance state to form a plurality of droplets in a gas containing an oxidant;

causing at least partial oxidation of the lower valance state ions to ions of higher valance state in the solution.

Preferable catalyst for the oxidation of cyclohexane to adipic acid for example comprises cobalt ions. The cobalt ions may be added to the first liquid either as cobaltous, or preferably as cobaltic ions. The level of catalyst in the first liquid can be varied in order to control the transient conversion. Higher amounts of ions, preferably cobaltic for faster response, favor the increase of transient conversion, while lower amounts of ions favor the decrease of transient conversion.

BRIEF DESCRIPTION OF THE DRAWING

The reader's understanding of this invention will be enhanced by reference to the following detailed description taken in combination with the drawing figures, wherein.

DETAILED DESCRIPTION OF THE INVENTION

Figure 1:
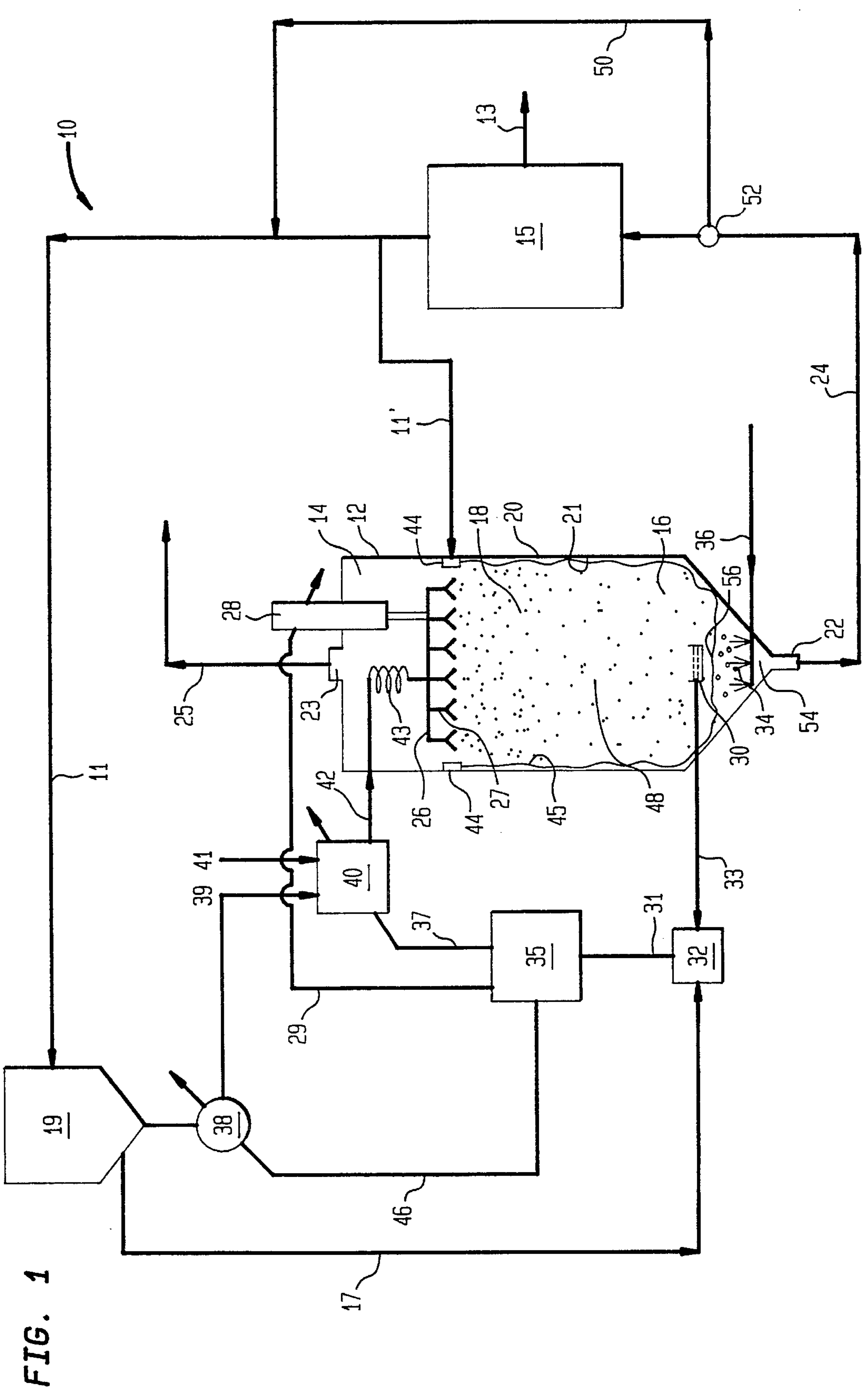
FIG. 1 illustrates schematically a preferred embodiment of the present invention, wherein control of transient conversion is achieved by changing the atomization distance through a movement of the atomizer.

As aforementioned, the present invention relates to methods of making intermediate oxidation products, wherein a first reactant incorporated in an atomized liquid reacts with a gas containing an oxidant, under controlled conditions. According to the present invention, the atomization conditions are subject to intricate critical controls and requirements as described and claimed hereinbelow.

As also aforementioned, reactions which are geared to produce intermediate products, especially in the case of oxidations, have not run under atomization conditions so far, since atomization promotes complete reactions to a final product. For example, oxidation of cyclohexane to adipic acid, or oxidation of p-xylene to terephthalic acid, have not been reported to be conducted under atomization conditions, and there is no incentive in the art to do so, since burning of cyclohexane to carbon dioxide has been expected to take place under such conditions. However, the inventors have discovered that in the presence of unexpected intricate critical controls and requirements of the instant invention, intermediate reaction or oxidation products, such as adipic acid, phthalic acid, isophthalic acid and terephthalic acid, for example, may be advantageously obtained under atomization conditions.

The present invention enables economic oxidation reactions at improved yield with reduced compression costs and investment, using proven catalyst systems, with reduced off-gas waste-stream discharge to the atmosphere, with reduced off-gas cleanup investment and costs, without solids plugging or buildup problems, with high utility, high conversion rates, and with reduced oxygen concentrations in the reaction chamber.

The ability to operate at lower oxygen concentration, made possible by this invention, with acceptable conversion rates in the reactor improves yield by reducing over-oxidations, and may eliminate safety (explosion) problems associated with operation in the explosive oxygen/fuel envelope by operating in the non-explosive oxygen/fuel envelope. In the current technology, reducing oxygen content below traditional levels would result in a non-economic reduction in reaction rate. In this invention, however, a significant increase in the ratio of gas-liquid interfacial area to liquid reaction mass—relative to current levels—offsets this rate reduction, thereby enabling economic operation at reduced oxygen concentration in the reactor.

Some of the key elements, which may be present singly or in any combination thereof, in the embodiments of the present invention, are:

- High productivity reaction volume;
- Elimination of reactor agitator and agitator seals;
- Efficient Catalyst Systems;
- Low off-gas waste-stream rate;
- Employment of an ultra-high ratio of gas/liquid interfacial area to liquid reaction volume;
- Employment of an ultra-low ratio of liquid reaction volume to liquid volume contained in the liquid-film diffusion zone attached to the gas interface;
- Variation and accurate control of the ratio of gas/liquid interfacial area to liquid reaction volume, and the ratio of liquid reaction volume to liquid volume contained in the liquid-film diffusion zone attached to the gas interface;
- Multi-parameter control of liquid reactant conversion;
- Multi-parameter control of liquid reaction mass temperature;
- Avoidance of solids buildup in the reactor;
- Internal condensation; and
- Easy recovery of high purity, high oxygen-concentration off-gas for recycle with low recompression requirements.

This invention provides a more productive reaction volume than does the conventional technology. Reaction chamber productivity per unit liquid reaction volume is increased due to the greatly enhanced mass transfer rates afforded by this invention, coupled, if so desired, with measures to maximize droplet loading in the reaction chamber. Droplet loading in the reaction chamber may be maximized according to the present invention, by employing internal condensation and generating ultra-small liquid reaction droplets. The droplet loading, measured as a percent of reaction chamber volume occupied by the totality of the droplets in the reaction chamber at any one time, is preferably maintained in the range of 1–40%. More preferably, droplet loading is maintained in the range of 5–30%. More preferably still, droplet loading is maintained in the range of 10–20%. Excessively high droplet loading can lead to sudden and uncontrolled coalescence, and is to be avoided. Too low droplet loading can lead to low reaction chamber productivity. The optimal control of droplet loading and initial droplet size minimizes the coalescence of droplets, while in the reaction chamber, optimizes the mass transfer of oxygen or other oxidant from the gas phase to the liquid phase, and maximizes the liquid reaction volume available to support the desired product formation.

As it will become clear in the course of this discussion, unlike in the conventional technology which utilizes sparging of oxidizing gases through mechanically agitated liquids containing reactants to be oxidized, there is no reaction chamber agitator and no agitator seals. This process simplification is made possible by the unique reaction environment provided by this invention, and is highly desirable as it reduces cost, investment, and improves plant utility compared to the conventional technology.

Since according to the present invention the oxidation is conducted within the droplets, which are in a liquid phase, the process still maintains the advantage of being able to employ efficient liquid-soluble catalyst systems, with the added advantage of attaining reaction conditions almost as efficient as those encountered in a homogeneous gaseous phase. Reactions in a gaseous phase would require costly and uncertain gas-phase catalysts or solid-phase catalyst systems.

Further, this invention enables a low off-gas waste-stream rate, if so desired, which reduces the off-gas waste-stream rate to the environment, and reduces off-gas cleanup investment and costs. The low off-gas waste-stream rate may be made possible with a near-stoichiometric gaseous oxygen feed combined with high conversion rates and/or chemical yields, for example.

In the conventional technology, reaction chamber non-condensible off-gas is commonly purged to the atmosphere without partial recycle back to the reaction chamber. This results in increased oxygen consumption and related cost, but is done to avoid high, non-economic recompression costs and investment. In the conventional technology, recompression costs and investment are high due to a high non-condensible load, and high recycle pressure requirement:

- high non-condensible load results from the relatively high chemical yield loss, and—in most instances—the use of air as the oxygen source;
- high recycle pressure is required to accommodate the high-pressure drop, subsurface sparging (into a liquid-filled reaction chamber) used in the conventional technology;
- the high-pressure drop is required, in the case of subsurface sparging, to overcome the liquid head in the reaction chamber and to provide high-power mixing; and
- high-power mixing is necessary, in the case of the conventional technology, to improve gas/liquid contacting and thereby accelerate the rate of oxygen transfer into the liquid phase.

Figure 11:
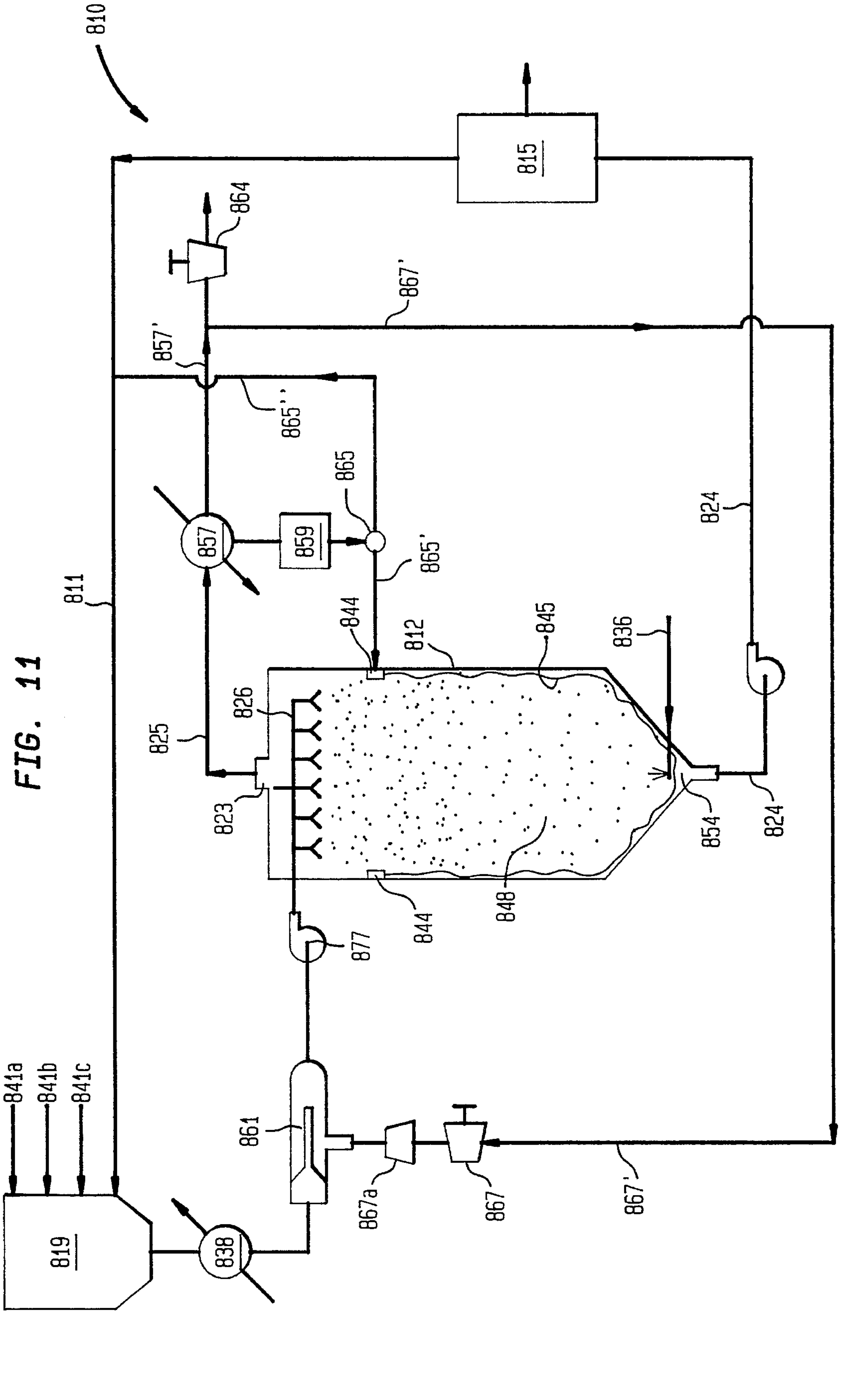
FIG. 11 illustrates schematically still another preferred embodiment of the present invention, wherein an eductor is utilized to recirculate non-condensible off-gases, a condenser is used to condense condensibles, and part of the condensibles return to the reaction chamber, where a thick film or curtain is formed for preventing solids buildup on the walls.

When condensation is employed at a stage before the pressure drop (internal condensation), as shown in the embodiment of FIG. 11 (before valve 864) for example, the increased oxygen consumption and related cost, and the high, non-economic recompression costs and investment associated with the conventional technology are avoided. According to this embodiment, it is possible to recycle oxygen-containing off-gas back to the reaction chamber with relatively low or no recompression requirement and cost. The recycle may be even eliminated without incurring significant adverse economic impact. When condensation is employed at such a stage, the recompression requirement is minimal-compared to the conventional technology—due to the low non-condensible off-gas rate, especially when near-stoichiometric oxygen feed is used. The low non-condensible off-gas rate is due to the combination of near-stoichiometric oxygen feed, with one or more of high conversion rate, high chemical yield, and internal condensation, enabled and provided for by the instant invention.

According to the instant invention, when near-stoichiometric oxygen feed is desired, it is achievable by the high conversion of the oxygen feed to the reaction chamber per pass, hence needing little recycle requirement. The high chemical yield results in low non-condensible by-product formation, thereby significantly reducing off-gas purge load generated in the reaction chamber. Reduced off-gas purge load in turn reduces oxygen purge from the reaction chamber. Reduced oxygen purge from the reaction chamber minimizes oxygen recycle requirement. The implementation of internal condensation further reduces recompression requirement, as internal condensation outside the reactor further reduces oxygen recycle required, and the implementation of internal condensation inside the reactor reduces oxygen recycle requirement further still. This internal condensation significantly reduces oxygen physical yield-loss. In the limit, internal condensation, complete oxygen conversion per pass, i.e., stoichiometric oxygen feed, and zero non-condensible by-product formation would result in zero oxygen physical yield loss and zero recompression requirement. Due to the low non-condensible off-gas rate made possible when internal condensation is employed, it is significantly less costly (compared to the conventional technology) to forego recycle.

In this invention, solids buildup in the reaction chamber is prevented by washing the walls of the reaction chamber with preferably cooler, preferably catalyst-free liquid solvent, or with preferably catalyst-free liquid reactant, or with a mixture thereof. All surfaces of the reaction chamber, or a certain portion of those surfaces prone to solids buildup, may be washed in this manner. The wash liquid may be sprayed onto the surfaces so washed, or may be generated in situ as a result of internal condensation. Solids buildup is prevented because the solids in contact with these surfaces are continuously washed out of the reaction chamber. Furthermore, reaction in the wash-liquid is greatly minimized by the lower temperature or absence of catalyst, the short hold-up-time or a combination thereof. All solids produced in the reaction chamber are removed from the reaction chamber with the wash liquid.

In the embodiments of this invention involving off-gas recycle, this invention provides means by which the recompression requirement can be greatly minimized or eliminated. Due to the small non-condensible off-gas rate associated with this invention, it is possible to educt the recycle off-gas into the reaction chamber using a liquid stream as the motive force.

In the conventional technology, gas sparging bubbles are dispersed in a continuous liquid-phase comprised of liquid reactants, liquid solvents, dissolved oxidation products and by-products, dissolved gases, and dissolved catalyst. A thin film of liquid is attached and surrounds each bubble, due to strong surface tension forces. While the thickness of the liquid-film is a function of many variables including, but not limited to, temperature and viscosity of the liquid solvent and liquid reactant, generally the thickness of the liquid-film is in the range of 0.05 inches to 0.0001 inches, and mostly in the range of 0.02 inches to 0.001 inches. Reactions can occur in this liquid-film and in the continuous-phase liquid surrounding this film. Oxidation products may in fact be preferentially produced in the film, relative to the surrounding liquid, depending on the nature of the diffusional resistance inhibiting the transfer of materials from the liquid film into the surrounding liquid. In any event, it is expected that a significant amount of reaction will occur in the liquid-film due to its immediate proximity to the gas-phase oxygen or other oxidant. In the conventional technology, the ratio of liquid reaction volume to liquid volume in the liquid-film is extremely high—typically, this would be several orders of magnitude. This extremely high ratio leads to two highly undesirable consequences:

First, it leads to gross non-homogeneities in the concentration of oxidation products between the two zones, with high localized product concentrations building up in the liquid-film. These high localized concentrations arise in the liquid-film in the conventional technology because a significant (perhaps even predominant) amount of reaction occurs in the liquid-film due to its immediate proximity to the gas-phase oxygen, and because oxidation products so formed in the liquid-film must necessarily increase in concentration—relative to the surrounding bulk liquid—to overcome diffusional resistance and migrate from the liquid-film out into the surrounding liquid. Furthermore, for a given production rate and conversion, the higher the ratio the higher the product concentration in the liquid-film. The worst consequence of high localized product concentration in the liquid-film in the conventional technology is that it leads directly to over-oxidation products. Over-oxidation results when already formed product continues to be exposed to reactive forms of oxygen. Over-oxidation in turn causes chemical yield loss, high product purification costs, and high waste disposal costs.

Second, it leads to poor utilization of the total available reaction volume. This results because the most productive reaction volume is that in closest proximity to the gas-phase oxygen. The reaction volume closest to the gas-phase oxygen is the liquid-film. At very high ratios the amount of volume occupied by the liquid-film is extremely small; hence, the poor utilization at high reaction volume.

This invention overcomes the aforementioned problems associated with the conventional technology by converting the reaction system to ultra-low ratio of liquid reaction volume to liquid volume in the liquid-film. This is the exact opposite of the conventional technology. In this invention, ultra-low ratios are obtained by converting the bulk stirred liquid phase to spray droplets of controlled small size suspended in the continuous gas-phase. The size of the droplets may be controlled such that the average radius of the droplet is preferably less than about 10 times the thickness of the diffusion film associated with the conventional technology. More preferably, the droplets should be controlled such that the average radius of the droplet is on less than about 5 times the thickness of the diffusion film associated with the conventional technology. More preferably still, the droplets are to be controlled such that the average radius of the droplet is less than about 1 time the thickness of the diffusion film associated with the conventional technology. By this method, the ratio can be decreased by orders of magnitude below that possible in the conventional technology. This is highly desirable because it enables a significant reduction in over-oxidation with concomitant reduction in impurity levels, reduction in purification costs and investment, and reduction in waste-stream load, without loss of production rate, and with more efficient utilization of liquid reaction volume in the reaction chamber (compared to the conventional technology).

Further, in the conventional technology, the ability to generate a high ratio of gas/liquid interfacial area to liquid reaction volume is constrained by natural effects (including liquid surface tension) to certain practical maximums. Heroic efforts, including high gas sparging rates and powerful agitation systems, have been employed to achieve operation near the upper maximum limit. The inventors theorized that a much higher ratio would be desirable, since it would facilitate the diffusion of oxygen reactant into a liquid film surrounding each gas bubble. This film is strongly attached to the bubble by strong surface tension forces. Reaction can occur in this film and in the continuous-phase liquid surrounding this film, and the ability to effect reaction in either zone is dependent on oxygen diffusion from the gas-phase into the film. In the conventional technology, higher diffusion rates may be only achieved by either increasing oxygen or other oxidant concentration in the gas passing through the liquid reaction phase, or by increasing the gas sparging rate. However, this is of very limited value, and only small improvements in diffusion rates may be made.

In contrast, according to this invention, huge improvements in diffusion rates may be made by using ultra-high ratios of gas/liquid interfacial area to liquid reaction volume, which are obtained by converting the bulk stirred liquid phase into spray droplets of controlled small size within a continuous gas-phase. For this purpose also, the size of the droplets should be controlled such that the radius of the droplet is on average preferably less than about 10 times the thickness of the diffusion film associated with the conventional technology. More preferably, the droplets should be controlled such that the radius of the droplet is on average less than about 5 times the thickness of the diffusion film associated with the conventional technology. More preferably still, the droplets are to be controlled such that the radius of the droplet is on average less than 1 time the thickness of the diffusion film. By this method, the ratio of gas/liquid interfacial area to liquid reaction volume can be increased by orders of magnitude above that possible in the conventional technology. This is highly desirable because it enables a significant reduction in the oxygen concentration in the gas-phase without loss of production rate (compared to the conventional technology), or, alternately, higher oxygen diffusion rates (hence higher production rates) at comparable oxygen concentration in the gas-phase.

The significant reduction in the oxygen concentration in the gas-phase, concurrent with still maintaining desirable high reaction rates, made possible by this invention, is extremely desirable because it acts to improve yield by reducing over-oxidation, improve safety by enabling operation further away from the oxygen/fuel explosive envelope, and minimize the amount of oxygen swept from the reaction chamber. Minimizing the amount of oxygen swept from the reaction chamber with other non-condensibles is desirable because it significantly reduces: (1) costly investment for waste off-gas environmental cleanup facilities, (2) waste off-gas discharges to the environment, and (3) very expensive, high maintenance, and potentially unsafe recompression requirements (all three of which cause problems in the conventional technology).

According to the present invention, variation and accurate control of the ratio of gas/liquid interfacial area to liquid reaction volume, and the ratio of liquid reaction volume to liquid volume contained in the liquid-film at the gas interface are provided. Since, in the present invention, the gas-phase is the continuous-phase, both ratios may be simultaneously controlled by controlling the average droplet size and the droplet size distribution spectrum. For small droplets, surface tension forces will pull the droplets into near spheres. For spherical droplets, the ratio of gas/liquid interfacial area to liquid reaction volume is inversely proportional to droplet diameter, and the ratio of liquid reaction volume to liquid volume contained in the liquid-film is directly proportional to droplet diameter. Consequently, ultra-high ratio of gas/liquid interfacial area to liquid reaction volume and ultra-low ratio of liquid reaction volume to liquid volume contained in the liquid-film can be simultaneously achieved and controlled by reducing droplet diameter to very small, controlled diameters. Specifically, as aforementioned, the size of the droplets is to be controlled such that the diameter of the droplet is on average less than 10 times the thickness of the liquid-film associated with the conventional technology. However, since droplets of increasingly small size contain diminimous reaction volume, and since little further advantage is to be gained in enhanced reaction rate and reduced overoxidation, preferably the droplets are to be controlled such that the diameter of the droplet is more than 0.5 times the thickness of the liquid-film associated with the conventional technology. More preferably the droplets are to be controlled such that the diameter of the droplet is more than 1 time the thickness of the liquid-film associated with the conventional technology. While the thickness of the liquid-film associated with the conventional technology is a function of many variables including, but not limited to, temperature and viscosity of the liquid solvent and liquid reactant, generally the thickness of the liquid-film is in the range of 0.05 inches to 0.0001 inch. In absolute terms the preferred average droplet diameter is in the range of 0.001 to 0.2 inch.

The ways to control average droplet diameters in atomization is well-known to the art, and it includes, but is not limited to, nozzle design, variable nozzle characteristics, pressure of atomized material, pressure of gas if gas is used for the atomization process, and the like.

The control of conversion within tight ranges and at desired levels is critical to a well run process. Erratic control leads to poor chemical and physical yields, process upsets, high purification costs, high trace impurity levels, high recycle requirements, lost utility, and reduced plant capacity. Too low conversion results in high recycle requirements, reduced physical yield, higher unit plant investment, higher unit energy consumption, and reduced plant capacity. Too high conversion leads to over-oxidation, poor chemical yields, high purification costs, high trace impurity levels, higher unit plant investment, and reduced plant capacity. In this invention, multiple ways are provided to control conversion. Conversion may be controlled at a desired level by manipulation of variables, either alone or in combination with each other. Some of these variables are:

- Oxygen concentration in the reaction chamber.
- The ratio of the concentrations of liquid solvent to liquid reactant in the liquid feed to the reaction chamber.
- The concentration of catalyst in the liquid feed to the reaction chamber.
- The hold-up time of the liquid feed in the reaction chamber.
- The size or diameter of the droplets in the reaction chamber.
- The temperature of the droplets.

According to this invention, conversion can be controlled, for example, by regulating the oxygen concentration in the reaction chamber. This is to be done by using oxygen as the limiting reagent. In this instance, the rate of oxygen feed to the reaction chamber would be increased or decreased as required to control conversion. Conversion is increased—holding all other parameters constant—by increasing oxygen feed rate, and thereby increasing oxygen concentration in the reaction chamber. Conversion is decreased—holding all other parameters constant—by decreasing oxygen feed rate, and thereby decreasing oxygen concentration in the reaction chamber.

Further, conversion is increased—holding all other parameters constant—by increasing the concentration of catalyst in the liquid feed to the reaction chamber, Conversion is decreased—holding all other parameters constant—by decreasing the concentration of catalyst in the liquid feed to the reaction chamber.

In addition, conversion is increased—holding all other parameters constant—by increasing the hold-up time of the liquid feed in the reaction chamber. Conversion is decreased -holding all other parameters constant—by decreasing the hold-up time of the liquid feed in the reaction chamber. Hold-up time of the liquid feed in the reaction chamber is controlled by varying the height of the gas-phase through the droplets fall. Hold-up time is increased by increasing the height, and decreased by decreasing the height. The height may be controlled in several ways. For example, it may be controlled by:

- Raising or lowering the height of the droplet spray nozzle or nozzles.
- Raising or lowering the height of a liquid pool at the liquid level at the end of the vertical reaction chamber. The height of the liquid pool can be determined and controlled by a variety of ways well known to the art.

Also, conversion is increased—holding all other parameters constant—by decreasing the size of the liquid droplets in the reaction chamber. Conversion is decreased—holding all other parameters constant—by increasing the size of the liquid droplets in the reaction chamber. Droplet size inversely affects conversion by controlling oxygen mass transfer into the liquid reaction media. Since the ratio of surface area to volume for a spherical droplet is inversely proportional to the diameter of a droplet, and since oxygen transport from the gas-phase is directly proportional to the surface area of a droplet, then the ratio of oxygen mass transport to the liquid volume contained in a droplet varies inversely with the diameter of the droplet. Therefore, the relative oxygen mass transfer for larger droplets is smaller than that for smaller droplets, and conversion is correspondingly reduced when all other parameters are held constant.

Because reaction rates are faster at higher temperatures, in this invention, conversion is increased—holding all other parameters constant—by increasing the temperature of the liquid droplets. Conversion is decreased—holding all other parameters constant—by decreasing the temperature of the liquid droplets in the reaction chamber.

According to this invention, the heat of reaction may be removed from the liquid reaction mass as vaporized liquid reactant and vaporized liquid solvent. These vaporized materials may be condensed either outside or inside the reaction chamber as it will be discussed hereinbelow.

Removal of heat inside the reaction chamber may be conducted for example by using condensation sprays, or condensation surfaces, or a combination thereof.

It should be stressed that internal condensation may take place either outside or inside the reaction chamber, as illustrated later. Internal condensation is condensation which takes place within the system, before the pressure is relieved. Internal or external (outside the pressurized system) should not be confused with inside (inside the reaction chamber) and outside (outside the reaction chamber) conversion.

In the case of condensation sprays, a portion of recycled liquid may be cooled in a heat exchanger, external to the reaction chamber, and be sprayed into the interior reaction chamber walls, or into the gas-phase of the reaction chamber, or both. In the case where said spray is directed onto the reaction chamber wall, and in the instance where reaction products are relatively insoluble in said spray, then streams after filtering out the reaction products are preferable. The absence of catalyst in this case is also important, because this absence and the relatively cold nature of the incoming streams act to prevent reaction in said spray on the interior wall of the reaction chamber. In the case where reaction products are relatively insoluble, this absence of reaction prevents the highly undesirable accumulation of solids on this surface. Condensation spray is effective because hot, condensible gases inside the reaction chamber condense on the cool, liquid surface. The amount of condensation induced in this manner may be controlled by regulating the flow rate, temperature, and position of the condensation spray. Increasing the flow rate, decreasing the temperature, and controlling the condensation spray so as to increase its liquid surface area act individually or in combination to increase the rate of condensation of the vaporized liquid containing the reactant and vaporized liquid solvent; the converse is also true.

Furthermore, in the case of condensation sprays, this invention provides both the means to control the liquid surface area of the condensation spray, and the means to prevent excessive contact of the reaction liquid spray with the condensation spray. Where condensation spray is directed against the side of the reaction chamber wall, the condensation surface area may be effectively controlled by manipulating the impingement position of the condensation spray nozzles on the side of the reaction chamber wall. Directing this spray higher up the side of the reaction chamber wall increases the condensation surface area. Conversely, directing it lower decreases the condensation area. Where the condensation spray is directed into the gas-phase of the reaction chamber, the condensation surface area may be effectively controlled by manipulating the size and amount of the droplets. Since the ratio of surface area to volume for a spherical droplet is inversely proportional to the diameter of a droplet, and since the cumulative volume of all of the droplets sprayed into the reaction chamber is fixed for a given flow rate, then the surface area may be easily and precisely increased—when all other parameters are held constant—by decreasing the droplet size. The converse is also true. Droplet size can be easily controlled using techniques well known to the art.

Furthermore, in the case of condensation sprays, it is critical to prevent excessive contact of the reaction liquid spray with the condensation spray. This is true because the condensation spray may not contain catalyst and is deliberately cooled well below the reaction temperature of the liquid reaction media. Excessive mixing of these two sprays could result in a significant reduction in condensation efficiency, reaction rate, or both. Excessive mixing is prevented in the first instance by positioning the spray nozzles so as to direct the condensation spray against the reaction chamber wall, and the liquid reaction spray into the gas-phase of the reaction chamber in a manner which minimizes wall contact. In the second instance, excessive mixing is prevented by selecting a spray nozzle for the condensation spray which produces a very small diameter droplet. This technique is effective because very small droplets do not readily mix with similar, smaller, or larger sized droplets, thereby preventing the undesired contact with the liquid reaction spray. Furthermore, producing a very small condensation spray droplet is highly efficient, from the standpoint of the desired condensation of vaporized liquid reactant and vaporized liquid solvent, because it increases the condensation surface area.

In the case of condensation sprays, and in the second instance where the condensation spray is directed into the gas phase of the reaction chamber and where excessive mixing is prevented by selecting a spray nozzle for the condensation spray which produces a very small diameter droplet, this invention provides a reaction system in which the liquid contents of the reaction chamber are comprised of two different droplet types: both types simultaneously occupy the same reaction environment and each is in close proximity to the other, but each type remains separate, each contains different concentrations of liquid solvent and liquid reaction chemicals, each type is at significantly different temperatures, and each performs different functions (namely, either condensation or reaction).

In the case where vaporized liquid reactant and vaporized liquid are condensed inside the reaction chamber on metal surfaces, this may be accomplished in the first instance by externally cooling the reaction chamber walls with an external cooling jacket through which is circulated a cooling medium, like cooling water; or, in the second instance, by providing a cooling coil or other cooling surface inside the reaction chamber through which is circulated a cooling medium, like cooling water. In the first instance, condensation occurs inside the reaction chamber when condensible gases come into contact with the externally cooled as al reaction chamber walls. The walls cooled by this method may be the vertical sides of the reaction chamber, or the top, or the bottom, or a combination thereof. In the second instance, condensation occurs when the condensible gases come into contact with the internal cooling coils or other cooling surfaces inside the reaction chamber.

According to this invention, non-condensible gases are swept away from the condensation surfaces (regardless of whether these condensation surfaces are the ones produced by the use of condensation sprays or by metal surfaces) by gaseous eddie currents inside the reaction chamber. These eddie currents may be induced by the combined liquid sprays inside the reaction chamber. The efficient removal of the non-condensible gases from the condensation surfaces is critical, because unless this is done, the condensation surfaces become blanketed by the non-condensibles, and the desired condensation is greatly diminished.

As already discussed, according to this invention, non-condensible reaction by-product gases may be purged from the reaction chamber through an overhead gas outlet or they may be purged out the bottom of the reaction chamber. In the former case, the small diameter liquid reaction droplets, or the small diameter liquid reaction droplets along with very small condensation spray droplets, produced according to the methods of this invention, fall to the bottom of the reaction chamber, where they coalesce and exit the reaction chamber. In the latter case, the small diameter liquid reaction droplets, or the small diameter liquid reaction droplets along with the very small condensation spray droplets, either fall to the bottom of the reaction chamber and coalesce there, or are swept by the non-condensible purge gases into a swirling vortex at the bottom of the reaction chamber and, thereby, are brought into extremely close proximity with the liquid, where they coalesce, as it will be discussed in more detail later. The extremely close contact so induced is sufficient to coalesce the small diameter liquid reaction droplets, or the small diameter liquid reaction droplets along with the very small condensation droplets, from the gas purge into the liquid phase. In both cases, therefore, the liquids exiting the bottom of the reaction chamber may remove both the reaction liquid spray, and the condensation spray, if present, from the reaction chamber.

As aforementioned, the controller, described in the description of the preferred embodiments, points the transient conversion in the droplets toward a predetermined conversion range. By this, it is meant that the controller is adapted to change one or more parameters, such as the preferable parameters dealt with as examples below, so that said change will favor a respective change in the transient conversion toward the predetermined range.

Depending on the reaction characteristics, some parameters or variables may be more or less effective in causing changes to the transient conversion. It is possible in some occasions that changes in one parameter may not be capable to bring the transient conversion within the predetermined range. In such cases, the controller is preferably adapted or programmed to select and change one or more additional variables in order to receive the desired result.

In the description of the preferred embodiments of the instant invention, it is assumed for purposes of clarity that the particular variable under consideration is capable by itself to bring the transient conversion within the predetermined range. This is generally true, provided that for a particular reaction, conducted in the devices and by the methods of this invention, the most efficient variable(s) has been selected to be controlled by the controller. It should be understood, however, that the selection of one or more additional variables is well within the scope of this invention.

It is important to note that according to this invention, appropriate overriding program rules may be used to overide the normal program of the controller, especially in occasions involving safety matters. For example, the temperature in the reaction chamber may preferably be monitored, and if it is found to start rising at a rate faster than a preset value, the controller should cause commensurate changes in one or more variables at a high enough rate to offset said rise timely, before any catastrophic outcome.

In addition, monitoring carbon monoxide and carbon dioxide in the off-gases is a prudent precaution, since unexpected or higher than normal amounts of carbon monoxide and/or carbon dioxide signify poorly controlled or uncontrolled oxidation. Similar overriding rules applied by the controller help prevent poor yields, conversions, and even explosions.

In the following description, the droplets have an average droplet diameter and they are produced at a desired first flow rate, the gas flows at a second flow rate, the droplets may contain volatile ingredients volatilizing at a volatilization rate, the first liquid contains a first reactant at a first content, the gas contains oxidant at a second content. The ratio of the oxidant to the inert or other gas determines the content of oxidant in the gas.

Also, in the following description, transient conversion is the conversion of first reactant to intermediate oxidation product as droplets of first liquid travel from the atomizer to the sample collector. It should be understood that information regarding the amounts of first reactant and oxidation product, if present, are monitored in the first liquid and they are provided to the computerized controller through the conversion monitor along with information regarding the percent moles of intermediate oxidation product in the sample collector. This whole information is collectively called transient conversion information. The analyses and/or computations from different lines are conducted by well known to the art techniques, and they have been omitted from the Figures for purposes of clarity. More specifically the transient conversion is defined as the ratio $(O^2-O^1)\times 100/R^1\times n$, where:

$O^1$ is the percent moles of intermediate oxidation product in the first liquid;

$O^2$ is the percent moles of intermediate oxidation product as provided to the conversion monitor by the sample collector;

$R^1$ is the percent moles of first reactant in the first liquid; and n is the number of moles of intermediate oxidation product produced when one mole of first reactant is completely converted to said intermediate oxidation product.

The inventors have recognized that in the case of atomizing reactors, transient conversion is of essence for controlling oxidation reactions, and not just the overall conversion over the whole process, as employed so far in the art. Control of transient conversion, not only helps in improving the yield, but in addition it helps in avoiding reactions leading to complete oxidation, combustion, or even explosion.

In one embodiment of the present invention, better shown in FIG. 1, there is depicted a device 10 for preparing an intermediate oxidation product from a first liquid containing a first reactant and a gas containing a second reactant. The device 10 comprises a reaction chamber 12, which chamber has an upper end 14, a lower end 16 and a reaction zone 18. The reaction chamber 12 also has a wall having an inside surface 21. The chamber 12 is preferably of cylindrical shape turning to conical at the vicinity of the lower end 16, and finally leading to a liquid outlet 22 connected to an outlet line 24. The outlet line 24 leads to a separator 15 where the intermediate oxidation products are separated from reactants following line, and unreacted reactants, usually containing various amounts of intermediate oxidation products, solvents, catalysts, and other adjuncts, return to a recirculation tank 19 through line 11. The separator may be as simple a device as a filter, or as complicated as a battery of tanks, washers, extractors, distillation columns, etc., suitable to each particular case. A by-pass line 50, connected to the system through a bypass valve 52 is used to by-pass the separator 15, if so desired.

At the vicinity of the upper end 14 of the reaction chamber 12, there is provided a gas outlet 23 leading to an outlet gas line 25.

There is also provided a liquid dispensing ring 44 on the wall 20 of the reaction chamber 12. The liquid dispensing ring 44 is connected to line 11', which provides liquid, preferably recovered. The ring 44 is adapted to distribute said liquid substantially uniformly on the inside surface 21 of the wall 20 in the form of a thick film or curtain 45.

The reaction chamber 12 is preferably adapted to withstand such temperatures and pressures, which are appropriate for the reaction conditions in the reaction chamber 12, and be suitable for the reactants and reaction products. Such materials and construction characteristics are well known to the art. For example, depending on the particular reaction, carbon steel, stainless steel, or Hastalloy may be required. In addition, the inside surface 21 may be protected by coatings or linings of vitreous or other materials.

Inside the reaction chamber 12, and preferably in the vicinity of the upper end 14, there is disposed an atomizer 26, preferably comprising a plurality of nozzles 27. The atomizer 26 is preferably of the airless type (does not need an atomizing gas for its operation). Airless atomizers are well known to the art. The atomizer 26 may be steady at a certain position of the reaction chamber 12, or it may be movable, preferably in an up/down mode. A driving mechanism 28, supporting the atomizer 26 is preferably connected to the reaction chamber 12 in the vicinity of the upper end 14. The driving mechanism 28 may be a hydraulic or pneumatic cylinder, or it may be of mechanical nature, such as one of the screw type, for example. It is mainly important that the driving mechanism 28 is adapted to move the atomizer 26 in a preferably up/down mode in a controllable manner, and without introducing leaks to the reaction chamber 12.

A gas inlet 34, preferably located in the vicinity of the lower end 16 of the reaction chamber 12, is connected to a gas inlet feed line 36, which provides the gas containing the second reactant.

In the vicinity of the lower part 16 of the reaction chamber 12, there is provided a sample collector 30, which is adapted to collect droplets of liquid and transfer them preferably as a miniature stream of liquid to a conversion detector (the word detector according to the present invention includes the meaning of monitor) 32 through sample line 33. The conversion detector 32 may also monitor the amount of first reactant and the amount of the intermediate oxidation product in the recirculation tank 19 through a sample line 17. This information along with information on the nature and quantity of what is added in line 41, for example, can accurately determine the amounts of intermediate oxidation product and first reactant going to the atomizer 26.

A heat exchanger 38 is adapted to provide recirculated reactant mixture from the recirculation tank 19 to a replenishment receptacle 40, through inlet line 39. The replenishment receptacle 40 is also provided with fresh reactants, catalysts, solvents, and other adjuncts necessary for the reaction in each particular case through inlet line 41. The replenishment receptacle 40 may be a container comprising temperature control (not shown) and a high pressure pump (not shown), which provides mixture made in the receptacle 40 to the nozzles 27 of the atomizer 26 through line 42 at a desired atomization temperature. Line 42 has a flexible, preferably coiled portion 43, so that it can follow any movements of the atomizer 26.

The device 10 also comprises a controller 35, preferably computerized, which is fed information regarding transient conversion of reactants to intermediate oxidation product from conversion detector 32 through input line 31, and it controls heat exchanger 38 through output line 27, the drive mechanism 28 through output line 29, and the replenishment receptacle 40 through output line 37.

The monitor or detector 32 may be any instrument which is adaptable to detect the intermediate oxidation product or products. It may, for example, comprise a chromatography apparatus, a UV spectrograph, an IR spectrograph, a visible light spectrograph, a mass spectrometer, a NMR instrument, a conductivity monitor, an ionization detector, a flame detector, any other suitable instrument, or a combination thereof.

In the case that the intermediate oxidation product is a non-volatile acid, it is preferable that the monitor or detector 32 comprises a HPLC (High Pressure/Performance Liquid Chromatography instrument) in combination with a UV monitor. It is also preferable that the HPLC instrument has more than one columns, so that if the separation time in a column is longer than desired, consecutive samples are introduced in different columns and a multiplicity of separations are conducted in parallel so that the interval between monitoring consecutive samples falls within desired limits. If it is desired to also analyze also non-polar organic moieties, it would be preferable to also include a gas chromatographic monitor or detector coupled with an appropriate monitor, such as an ionization monitor, for example.

The method and the devices of the instant invention are particularly suitable for oxidation reactions of organic compounds, wherein the major portion of the oxidation product is an oxidation intermediate different than CO, $CO_2$, or a mixture thereof. One of the reasons why this is so, is that, due to the intricate criticalities of the present invention, the reaction rates, reaction homogeneity, yield, and other important properties are considerably improved, while in the absence of said criticalities complete oxidation to $CO/CO_2$ would take place. Actually, the same conditions of atomization without said criticalities, are presently used in combustion engines of automobiles and other devices, to substantially completely oxidize (combust or burn in other words) organic compounds such as gasoline to a mixture of $CO/CO_2$.

In contrast, according to the present invention, if for example, the first reactant is cyclohexane, the major portion of the oxidation product may be substantially cyclohexanol, cyclohexanone, cyclohexylhydroperoxide, caprolactone, adipic acid, the like, and mixtures thereof. Organic acids are preferable oxidation products.

The operation of this, as well as the other embodiments of the instant invention, will be discussed for any non-destructive oxidation encompassed by the claims, and at the same time it will be exemplified, by using cyclohexane as a first reactant, oxygen as the oxidant in the gas, and adipic acid as the intermediate oxidation product. The term "intermediate oxidation product", as aforementioned, signifies that the oxidation stops before substantially oxidizing the first reactant to carbon monoxide, carbon dioxide, or mixtures thereof.

In operation of this embodiment, a first liquid containing the first reactant, cyclohexane for example, enters the reaction chamber 12 through line 42 in a manner that it is atomized by the atomizer 26 and nozzles 27, in a manner to form a plurality of droplets 48. The first liquid enters the atomizer at a desired atomization temperature, which in the case of cyclohexane is preferably in the range of 50°–150° C., more preferably in the range of 80°–130° C., and even more preferably in the range of 90°–120°. Atomization temperature of the first liquid is the temperature of the liquid just before it is atomized. The temperature of the just formed droplets may be the same or different than the atomization temperature. In the case of cyclohexane, the first liquid also preferably contains a solvent, such as acetic acid, for example, a catalyst, such as a cobalt compound, soluble in the first liquid, for example, and an initiator, such as cyclohexanone, methylethylketone, acetaldehyde, the like, and mixtures thereof, for example. The pressure in the case of oxidation of cyclohexane to adipic acid should preferably be high enough to maintain the cyclohexane, solvents, initiators, etc., substantially in the liquid state. Although pressures even in excess of 1,000 psia are possible, pressures in the range of 100 to 400 psia are preferable, and pressures in the range of 150 to 300 psia more preferable.

The atomizer 26 is initially preferably placed, by the drive mechanism 28, at a low position close to the lower end 16 of the reaction chamber 12 (although in FIG. 1 the atomizer 26 happens to have a position in the vicinity of the upper end 14 of the reaction chamber 14 ), at a distance from a mass of a second liquid 54, which has a second surface 56, and which is collected and disposed of at the lower end 16 of the reaction chamber 12 through liquid outlet 22. The second liquid is a combination of coalesced droplets 48 and liquid from the thick film or curtain 45. The distance between the nozzle of the atomizer which is closest to the surface 56 of the mass 54, and the surface 56 of the mass of the second liquid 54 is defined as the atomization distance. If the second liquid 54 has been removed completely from the reaction chamber 12, the atomization distance is defined as the distance between the nozzle of the atomizer which is closest to the point where the liquid outlet 22 meets the reaction chamber, and that point. The atomization distance at the beginning of the operation is preferably about one third to one fourth of the maximum atomization distance. The maximum atomization distance is the atomization distance when the atomizer is as far away from the surface 56 of the second liquid mass 54 as the design of the device 10 and the atomizer 26 allows. The atomizer has the maximum atomization distance in FIG. 1.

At the same time that the first liquid is being atomized, a gas containing the oxidant, preferably oxygen in the case of cyclohexane, enters the chamber 12 through the gas inlet feed line 36, in the vicinity of the lower end 16 of the chamber 12. The gas, in addition to the oxidant, may also contain rather inert gases, such as nitrogen and/or carbon dioxide for example. Off gases mixed with vapors of reactants, solvents, mist, and the like exit the reaction chamber through outlet gas line 25 and are treated as it will exemplified at a later section.

As the droplets fall in a downwardly direction from the atomizer 26, they start reacting with the oxidant, which is oxygen for example. The second liquid 54 is removed, preferably continuously, through the liquid outlet 22, and it is pumped (pump not shown) through liquid outlet line 24 to a separator 15, where the intermediate oxidation product, adipic acid for example, is separated from the liquids by techniques well known to the art. In some occasions, other by-products of the oxidation may also be removed in the separator, if so desired. Reactants, solvents, catalysts, and the like, return through line 11 to the recirculation tank 19.

Part of the second liquid, after the above product and/or by-product removal treatment, may be directed to the liquid dispensing ring 44, through line 11', if so desired, where it is dispensed in the form of the thick film or liquid curtain 45, and covers the inside surface 21 of the wall 20 of the reaction chamber 12. The temperature of this film, when it is dispensed from the dispensing ring 44 is arranged to be lower than the atomization temperature. In the case of cyclohexane to adipic acid, for example, it is preferably in the range of 20° to 80° C., and more preferably in the range of 20° to 40° C. At this lower temperature, no appreciable reaction takes place, and any droplets coalescing onto the film do not have much effect to the process. Any solid products which are insoluble in the droplets are washed down by the liquid curtain 45, and they form the second liquid 54 along with the coalesced droplets 48, as already mentioned. Thus, no sticking of solids takes place on the inside surface 21 of the wall 20. It should be noted that unrecycled liquids, which might be just solvents, or just reactants with or without catalysts or other adjuncts, or other liquids, or any combination thereof, may replace or supplement the recycled liquid coming from line 11'. If so desired, the second liquid transported in line 24 may by-pass the separator 15 through by-pass valve 52 and by-pass line 50 either partially or totally. This option may be utilized, especially at the beginning of the operation, if the transient conversion is under a desired pre-coalescing transient conversion level.

Measures are taken for the level or surface 56 of second liquid 54 not to move over the point at which the sample collector 30 is positioned, to prevent flooding of the sample collector 30 with second liquid 54, which will produce false sampling. Monitoring a liquid level is very well known to the art and may be conducted with any suitable type of "liquid level monitor", available in the market. The liquid level monitor is then arranged to control the supply of liquids entering the reaction chamber 12 as curtain 45 though line 11', as droplets through the atomizer 26, or exiting the reaction chamber 12 as second liquid 54 through outlet liquid line 24, or any combination thereof, so as to keep the level or surface 56 of the second liquid mass 54 within desired limits under the sample collector 30. Such an arrangement is very simple, and it is not shown in FIG. 1 for clarity purposes. Higher supply of liquids through line 11' and the atomizer will cause the level of surface 56 to be raised, while lower supply will have the opposite effect. Similarly, higher removal rate through line 24 will cause the level of or surface 56 to be lowered, while lower removal rate will have the opposite effect.

A part of the droplets 48 fall into the sample collector 30, just above the surface 56 of the second liquid mass 56, from where, they are directed to the conversion detector or monitor 32, to be analyzed regarding transient conversion. If solids are present in the droplets, care should be taken to prevent clogging of liquid transporting lines by use of appropriate dilution, and the like. As aforementioned, in the case of adipic or other acid formation, it is preferable that the monitor 32 comprises a chromatography apparatus, which more preferably is a High Performance (or Pressure) Liquid Chromatography apparatus (HPLC). This apparatus, as also mentioned earlier, may preferably have an adequate number of columns, so that it is capable of making a respective number of overlapping determinations of the intermediate oxidation product present in the droplets just before they coalesce into the mass of the second liquid 54, so that the transient conversion of the first reactant to intermediate reaction product is checked as frequently as desired in each particular case. If the column, for example, separates the intermediate oxidation product in 8 minutes, and the desired interval between determinations is 2 minutes in a particular case, four columns are needed.

Sampling of the liquid in the recirculation tank 19, may also be desirable, and it may be carried out in the same detector 32, through line 17, or by means of another detector (not shown).

The information obtained in the conversion detector or monitor 32 is fed to computerized controller 35 through its input line 31, where it is processed by well known to the art techniques. The controller 35 controls the heat exchanger 38 through its output line 46, which along with the temperature of the liquids provided through line 41, determines the temperature in the replenishment receptacle 40, which temperature is substantially the same as the atomization temperature for all practical purposes. Controller 35 through its output line 37, controls the feed rate of first liquid through line 42. In addition, controller 35, through its output line 29, controls the drive mechanism 28.

If the transient conversion is above a range called according to this invention "pre-coalescing transient conversion range" because it represents the transient conversion just before the droplets coalesce on to the second liquid 54, the drive mechanism 28 is ordered by the controller 35 to lower the level of atomizer in a manner that the atomization distance, as defined above, decreases. The change of atomization distance is preferably conducted in increments, preferably in the range of 10 to 50% of the atomization distance at the particular time, and more preferably in the range of 10 to 30%. However, other ranges may be more appropriate, depending on the particular conditions, materials, previous determination, and the like. For example, if a 10% decrease in atomization distance is found not to have an appreciable result, the following increment may be 30%, for example. On the other hand, if a 10% decrease in the atomization distance results in an overwhelming change in transient conversion, the next increment may be 5%, for example, until the conversion falls within the desirable range, and preferably in the most desirable range. It should be pointed out again, however, that the desirable ranges may change, depending on materials, conditions, etc. The distance between the sample collector 30 and the level or surface 56 of the second liquid mass 54 is preferably in the range of 5–10% of the maximum atomization distance.

In the case of oxidation of cyclohexane to adipic acid, for example, the preferred pre-coalescing transient conversion range is 5–80%, more preferably 10–70%, and even more preferably 20–60%.

After the transient conversion is found to be within the most desired range (20–60%, for example, in the case of cyclohexane to adipic acid under certain conditions), it continues to be monitored with a goal in most cases to stay somewhere in the vicinity of the middle value of said most desired range (about 40% for example). Continuous monitoring and control are highly desirable, since the conditions in the reaction chamber may vary, causing changes in the transient conversion values.

It should be noted that if the reaction is very slow for some reason, or if so desired, partial or total recirculation (not shown) directly from line 24 to line 42 is advisable, with or without additional feeding of line 42 from replenishment receptacle 40.

The pre-coalescing conversion can be also calculated or measured from samples of the second liquid, after taking into account any factors which change the concentration of the reaction product in the droplets.

Figure 2:
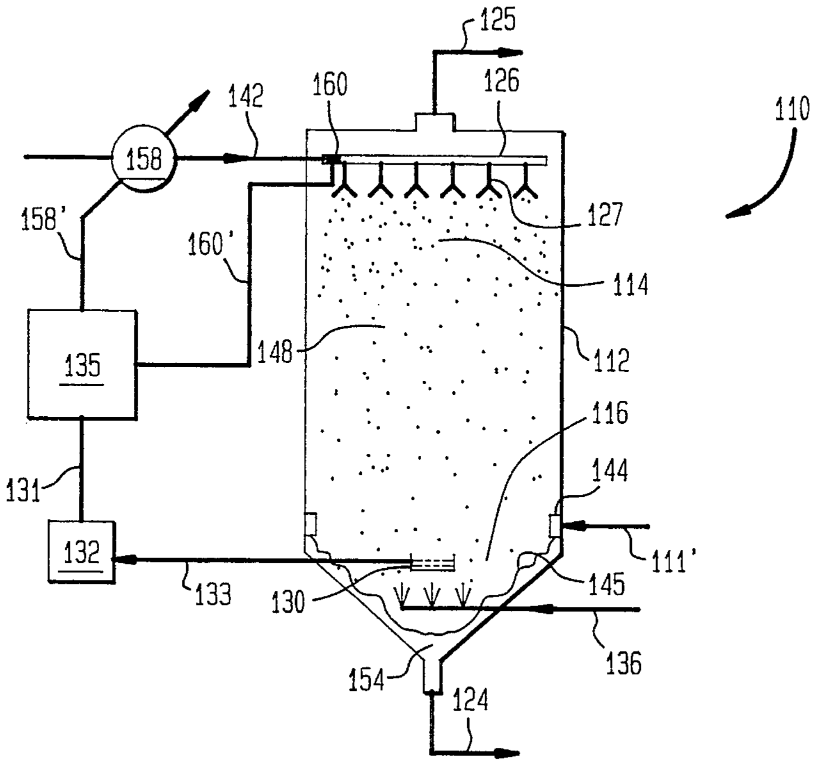
FIG. 2 illustrates schematically another preferred embodiment of the present invention, wherein control of transient conversion is achieved by changing the atomization temperature.

In another embodiment of the present invention, better shown in FIG. 2, the reaction chamber 112 is provided with an atomizer 126 in the vicinity of its upper end 114, and a sample collector 130 positioned in the vicinity of its lower end 116. There is also provided a supplementary heat exchanger 158 and a temperature measuring device, such as a thermocouple 160, for example. The liquid dispensing ring 144 is shown at the beginning of the conical portion of the reactor, but it may take any position on the wall of the reactor, or it may be omitted all together. The same holds true for all embodiments of the present invention. The sample collector 130 is connected to the conversion monitor or detector 132 through line 133 for providing samples of droplets 148 trapped in the collector just (and coalesced, of course in the collector) before they coalesce onto the second liquid mass 154. The thermocouple 160 and the conversion monitor or detector 132 are connected, preferably electrically, to the controller 135 through input lines 160' and 131, respectively. In turn, the controller 135 is connected, preferably electrically, to the supplemental heat exchanger 158 through output line 158' in order to control said supplemental heat exchanger 158. For purposes of clarity, basically only the elements of the device 110, which illustrate this embodiment and its operation, are shown.

In operation of this embodiment, the first liquid containing the first reactant, cyclohexane for example, enters the reaction chamber 112 through line 142 in a manner that it is atomized by the atomizer 126, in a manner to form a plurality of droplets 148.

At the same time that the first liquid is being atomized, a gas containing the oxidant, preferably oxygen in the case of cyclohexane, enters the chamber 112 through the gas inlet feed line 136, in the vicinity of the lower end 116 of the chamber 112. The gas, in addition to the oxidant, may also contain rather inert gases, such as nitrogen and/or carbon dioxide for example. Off gases mixed with vapors of reactants, solvents, mist, and the like exit the reaction chamber through outlet gas line 125 and are treated as it will exemplified at a later section.

As the droplets fall in a downwardly direction from the atomizer 126, they start reacting with the oxidant, which is oxygen for example. The second liquid 154 is removed, preferably continuously, through the liquid outlet line 124 as in the previous embodiment.

Part of the second liquid, after removal of the oxidation product and/or by-products, may be directed to the liquid dispensing ring 144, through line 111', if so desired, where it is dispensed in the form the thick film or liquid curtain 145, as in the previous embodiment.

A part of the droplets 148 fall into the sample collector 130, from where, they are directed to the conversion detector or monitor 132, to be analyzed regarding transient conversion.

The information obtained in the conversion detector or monitor 132 is fed to computerized controller 135 through its input line 131, where it is processed by well known to the art techniques. Also, the atomization temperature from thermocouple 160 is fed to the computerized controller 135. The controller 135 controls the heat exchanger 158 through its output line 158'.

If the transient conversion is above the pre-coalescing transient conversion range, as earlier defined, the heat exchanger is ordered by the controller 135 to lower the atomization temperature, monitored by thermocouple 160. Similarly, if the transient conversion is under the "pre-coalescing transient conversion range", according to this invention, the heat exchanger is ordered by the controller 35 to increase the atomization temperature. The upper and lower limits of the atomization temperature depend on the reactants, conditions of the reaction, and the like. For example, in the case of oxidation of cyclohexane to adipic acid, the upper limit should preferably be maintained not higher than 170° C., and more preferably not higher than 150° C., while the lower limit should preferably maintained not lower than 50° C., and more preferably not lower than 70° C.

The change of atomization temperature is preferably conducted in increments, preferably in the range of 5 to 10% of the atomization temperature at the particular time.

After the transient conversion is found to be within the most desired range (20–60%, for example, in the case of cyclohexane to adipic acid for example under certain conditions), it continues to be monitored with a goal in most cases to stay somewhere in the vicinity of the middle value of said most desired range (about 40%, for example). As in the previous embodiment continuous monitoring and control are highly preferable, since the conditions in the reaction chamber may vary, causing changes in the transient conversion values.

Figure 3:
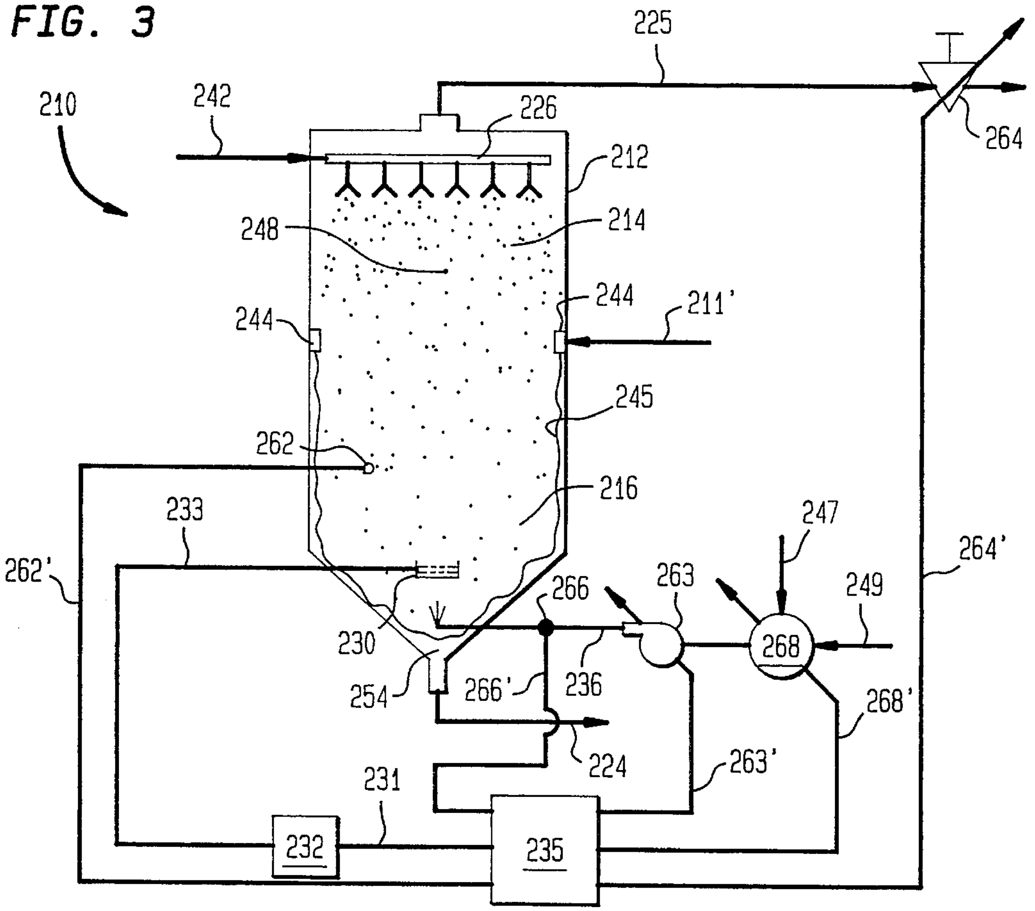
FIG. 3 illustrates schematically still another preferred embodiment of the present invention, wherein control of transient conversion is achieved ether by changing the pressure in the reaction chamber, or by changing the second flow rate, or by changing the second content.

In a different embodiment of the present invention, better shown in FIG. 3, the reaction chamber 212 is provided with an atomizer 226 in the vicinity of its upper end 214, and a sample collector 230 positioned in the vicinity of its lower end 216. There is also provided a pressurizing pump 263 communicating with the reaction chamber 212 through line 236, a flow meter 266 in the line 236, a gas mixing valve 268 connected on one side to an oxidant feed line 247 and an other gas line 249, and a pressure measuring device, such as a pressure gauge 262, for example for monitoring the pressure inside the reaction chamber 212. The liquid dispensing ring 244 is shown at about the middle of the wall of the reaction chamber 212, but it may take any position on the wall, or it may be omitted all together. The sample collector 230 is connected to the conversion monitor or detector 232 through line 233 for providing samples of droplets 248 trapped in the collector, just (and coalesced, of course, in the collector) before they coalesce onto the second liquid mass 254. The pressure gauge 262, the flow meter 266, and the conversion monitor or detector 232 are connected, preferably electrically, to the controller 235 through input lines 262', 266', and 231, respectively. In turn, the controller 235 is connected, preferably electrically, to the pressurizing pump 263 through output line 263', to the gas mixing valve 268 through output line 268', and to valve 264 through output line 264'. The controller 235 is adapted to control the pressurized pump 263, the gas mixing valve 268, and the valve 264. For purposes of clarity, basically only the elements of the device 210, which illustrate this embodiment and its operation, are shown.

In operation of this embodiment, the valve 264 is initially closed or turned to the off position. The gas mixing valve 268 is regulated to deliver a desired ratio of oxidant to inert gas (which ratio determines the content of oxidant in the total gas, defined earlier as the second content) to the pressurizing pump 263, obtained from lines 247 and 249, respectively. The pressurizing pump is then turned on until the desired pressure is attained in the reaction chamber 212. In sequence, with the pressurizing pump still on, the valve 264 is opened to such a degree that the desired pressure is maintained in the reaction chamber. If the flow rate (second flow rate being the flow rate of the gas, as defined above), as measured from the flowmeter 266, is too high, the pump is turned to a lower speed and the valve 264 is turned to a less open position in a manner to maintain the desired pressure at a lower second flow rate. This is continued until both the pressure and second flow rate attain desired values. If the second flow rate, as measured from the flowmeter 266, is too low, the pump is turned to a higher speed and/or the valve 264 is turned to a more open position in a manner to maintain the desired pressure at a higher second flow rate. This is continued until both the pressure and the second flow rate attain desired values.

After both pressure and the second flow rate have attained their initial desired values, the first liquid, after having been heated to the atomization temperature as described before, which liquid contains the first reactant, cyclohexane for example, enters the reaction chamber 212 through line 242 in a manner that it is atomized by the atomizer 226, and forms a plurality of droplets 248.

At the same time that the first liquid is being atomized, the mixed gas containing the oxidant, preferably oxygen in the case of cyclohexane, enters the chamber 212 through the gas inlet feed line 236, in the vicinity of the lower end 216 of the reaction chamber 212. The desired ratio of the gases (defining the second content as discussed earlier) depends on the reaction and conditions, and it may have any value suitable for the circumstances. In most cases the preferable oxidant is oxygen and the other gas is an inert gas, such as nitrogen or carbon dioxide, for example. Off gases mixed with vapors of reactants, solvents, mist, and the like exit the reaction chamber 212 through outlet gas line 225, and are treated as it will be exemplified at a later section.

As the droplets fall in a downwardly direction from the atomizer 226, they start reacting with the oxidant, which is oxygen for example. The second liquid 254 is removed, preferably continuously, through the liquid outlet line 224 as in the previous embodiments.

Part of the second liquid, after removal of the oxidation product and/or by-products, in the separator 15 shown in FIG. 1, may be directed to the liquid dispensing ring 244, through line 211', if so desired, where it is dispensed in the form the thick film or liquid curtain 245, as in the previous embodiments.

A part of the droplets 248 fall into the sample collector 230, from where, they are directed to the conversion detector or monitor 232, to be analyzed regarding transient conversion.

The information obtained in the transient conversion detector or monitor 232 is fed to computerized controller 235 through its input line 231, where it is processed by well known to the art techniques. Also, the pressure within the reaction chamber from gauge 262, and the flow rate of gases (second flow rate) through line 236 measured by the flow meter 266 are fed to the computerized controller 235 through input lines 262' and 266', respectively. As aforementioned, the controller 235 controls the pressurizing pump 263 through its output line 263', valve 264 through its output line 264', and gas mixing valve 268 through its output line 268'.

Controlling the pressurizing pump means that the controller is adapted to change the pressure and flow output of the pressurizing pump based on data received from input lines 231, 266', and 262', said data being processed according to a desired program. Controlling the valve 264 means that it is adapted to open/close said valve 264 to a desired degree based on data received from input lines 231, 266', and 262', said data being processed according to a desired program. Controlling the gas mixing valve 268 means that it is adapted to regulate said valve 268 in a manner to feed the pressurizing pump 263 with a mixture of oxidant provided by line 247 and other (such as inert for example) gas provided by line 249, so that the mixture has a desired weight ratio, based on data received from input lines 231, 266', and 262', said data being processed according to a desired program. Programming computerized controllers is well known to the art.

As it can be seen in FIG. 3, two elements which can determine the pressure inside the reaction chamber 212, as well as the second flow rate in this embodiment, are the pressurizing pump 263 and the valve 264. Other elements in line 225, such as condensers (not shown), gas recirculation assemblies (not shown), and the like for example, may also influence the pressure, mostly temporarily, but they have been omitted from FIG. 3 for purposes of clarity. They will be discussed at a later section. The more gas the pressurizing pump dispenses to the reaction chamber 212, and the more closed the valve 264 is the higher the pressure inside the reaction chamber. The less gas the pressurizing pump dispenses to the reaction chamber 212, and the more open the valve 264 the lower the pressure inside the reaction chamber. Of course, the flow or delivery rate of gas by the pressurizing pump 263 and the degree of opening of the valve 264 have to be coordinated in order to achieve a desired pressure inside the reaction chamber.

The data received in the computerized controller 235 may be used after being processed in a number of ways, or combinations thereof, to control the transient conversion and maintain it within the pre-coalescing transient conversion range.

One way is to vary the flow rate of the gas (second flow rate) entering the reaction chamber 212 through line 236. If the transient conversion, as measured in the transient conversion monitor or detector 232 has a higher value than the desired pre-coalescing transient conversion range, the computerized controller 235 orders the pressurizing pump to decrease the second flow rate as measured by the flowmeter 266. At the same time, the valve 264 is ordered by controller 235 to attain a somewhat more closed or restricted position so that the pressure inside the reaction chamber 212, as measured by the pressure gauge 262, tends to remain within the desired range. This is continued until the second flow rate has attained a newly desired value, and pressure is within the desired range. If the transient conversion, as measured in the conversion monitor or detector 232 has a lower value than the desired pre-coalescing transient conversion range, the computerized controller 235 orders the pressurizing pump to increase the second flow rate as measured by the flowmeter 266. At the same time, the valve 264 is ordered by controller 235 to attain a somewhat more open position, so that the pressure inside the reaction chamber 212, as measured by the pressure gauge 262, tends to remain within the desired range. This is continued until the second flow rate has attained a newly desired value and the pressure is within the desired range. The second flow rate changes (increase or decrease) from one value to a newly desired value should preferably be in increments, preferably in the range of 5–20% and more preferably in the range of 510%. Also, changes should preferably be ordered by the computerized controller in time intervals long enough to contain at least one new transient conversion measurement in the conversion monitor or detector 232.

If the transient conversion under the newly attained second flow rate does not fall within the predetermined pre-coalescing transient conversion range, the same process is repeated until the transient conversion finally falls within the desired transient conversion range.

Another way is to vary the ratio of the oxidant to the inert or other gas entering the reaction chamber 212 through line 236. If the transient conversion, as measured in the conversion monitor or detector 232 has a higher value than the desired pre-coalescing transient conversion range, the computerized controller 235 orders the gas mixing valve 268 to decrease said ratio. If the transient conversion, as measured in the conversion monitor or detector 232 has a lower value than the desired pre-coalescing transient conversion range, the computerized controller 235 orders the gas mixing valve 268 to increase said ratio. The ratio changes (increase or decrease) from one value to a newly desired value should preferably be in increments, preferably in the range of 5–20% and more preferably in the range of 5–10%. Also, changes should preferably be ordered by the computerized controller in time intervals long enough to contain at least one new transient conversion measurement in the conversion monitor or detector 232.

Still a different way is to vary the pressure of the gas in the reaction chamber 212 in many occasions, where increase in pressure increases reactivity to a substantial degree. If the transient conversion, as measured in the transient conversion monitor or detector 232 has a higher value than the desired pre-coalescing transient conversion range, the computerized controller 235 orders the pressurizing pump slow down. At the same time, the valve 264 is ordered by controller 235 to attain a somewhat more open position so that the second flow rate, as measured by the flow meter 266, tends to remain within the desired range. This is continued until the pressure has attained a newly desired value, and the second flow rate is within the desired range. If the transient conversion, as measured in the conversion monitor or detector 232 has a lower value than the desired pre-coalescing transient conversion range, the computerized controller 235 orders the pressurizing pump speed up. At the same time, the valve 264 is ordered by controller 235 to attain a somewhat more closed position so that the second flow rate, as measured by the flow meter 266, tends to remain within the desired range. This is continued until the pressure has attained a newly desired value, and the second flow rate is within the desired range. The pressure changes (increase or decrease) from one value to a newly desired value should preferably be in increments, preferably in the range of 2–20% and more preferably in the range of 5–10%. Also, changes should preferably be ordered by the computerized controller in time intervals long enough to contain at least one new transient conversion measurement in the conversion monitor or detector 232.

If the transient conversion under the newly attained pressure does not fall within the predetermined pre-coalescing transient conversion range, the same process is repeated until the transient conversion finally falls within the desired transient conversion range.

Figure 4:
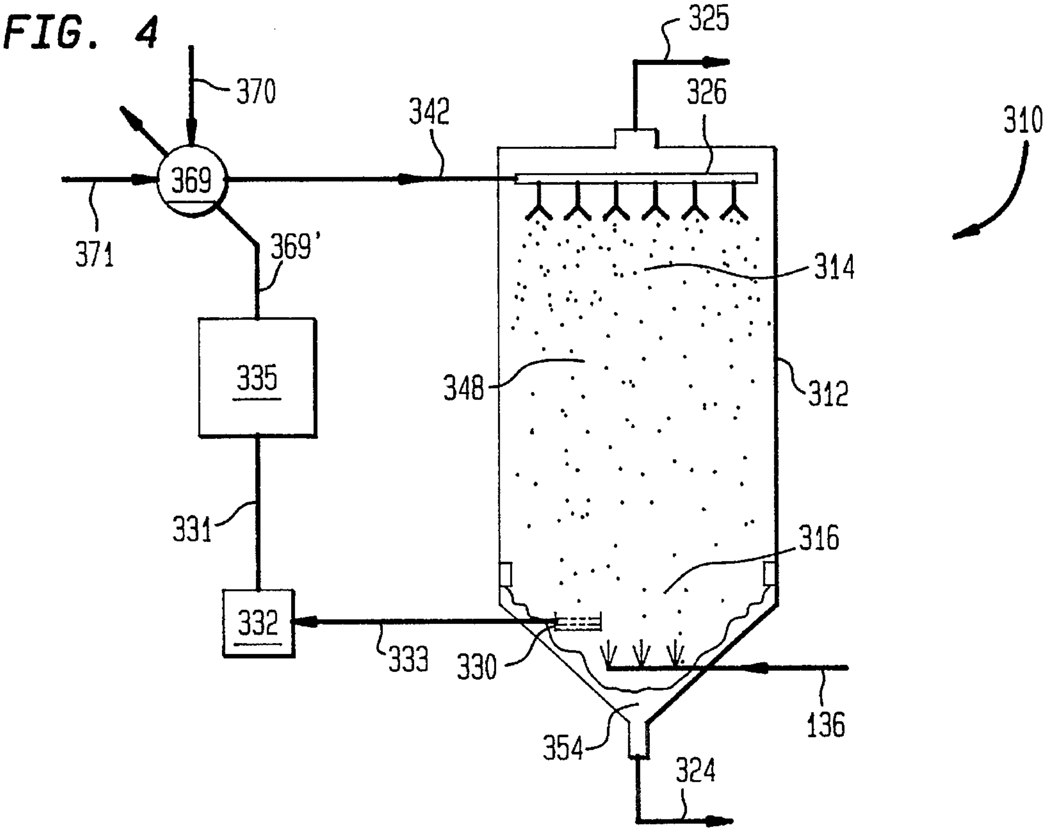
FIG. 4 illustrates schematically still another preferred embodiment of the present invention, wherein control of transient conversion is achieved by changing the first content.

In another embodiment of the present invention, better shown in FIG. 4, the reaction chamber 312 is provided with an atomizer 326 in the vicinity of its upper end 314, and a sample collector 330 positioned in the vicinity of its lower end 316. There is also provided a reactant mixing valve 69, which is adapted to mix first reactant from line 370 and other liquids from line 371 in order to produce the first liquid in line 342 having a first content of first reactant. The sample collector 330 is connected to the conversion monitor or detector 332 through sample line 333 for providing samples of droplets 348 trapped in the collector just (and coalesced, of course in the collector) before they coalesce onto the second liquid mass 354. The conversion monitor or detector 332 is connected, preferably electrically, to the controller 335 through input line 331 for transferring transient conversion information. In turn, the controller 335 is connected, preferably electrically, to the reactant mixing valve 369 through output line 369' in order to control said reactant mixing valve 369. For purposes of clarity, basically only the elements of the device 310, which illustrate this embodiment and its operation, are shown.

In operation of this embodiment, first reactant from line 370 and other liquids from line 371 are mixed in proportions regulated by the reactant mixing valve 369, in order to produce the first liquid in line 342 so that said first liquid has a first content of first reactant. The liquids from line 371 may contain solvents, catalysts, promoters, initiators, recycled ingredients, first reactant, and the like. If the liquids from line 371 contain first reactant, the content of these liquids in first reactant has to be taken into account in the determination of the first content of first reactant in line 342, so that the reactant mixing valve 369 allows accordingly less first reactant from line 370. The first liquid containing the first reactant, cyclohexane for example, in a first content, enters the reaction chamber 312 through line 342 in a manner that it is atomized by the atomizer 326, and forms a plurality of droplets 348.

At the same time that the first liquid is being atomized, a gas containing the oxidant, preferably oxygen in the case of cyclohexane, enters the chamber 312 through the gas inlet feed line 336, in the vicinity of the lower end 316 of the chamber 312. The gas, in addition to the oxidant, may also contain rather inert gases, such as nitrogen and/or carbon dioxide, for example. Off gases mixed with vapors of reactants, solvents, mist, and the like exit the reaction chamber 312 through outlet gas line 325 and are treated as it will exemplified at a later section.

As the droplets fall in a downwardly direction from the atomizer 326, they start reacting with the oxidant, which is oxygen for example. The second liquid 354 is removed, preferably continuously, through the liquid outlet line 324 as in the previous embodiments.

A part of the droplets 348 fall into the sample collector 330, from where, they are directed to the conversion detector or monitor 332, to be analyzed regarding transient conversion.

The information obtained in the conversion detector or monitor 332 is fed to computerized controller 335 through its input line 331, where it is processed by well known to the art techniques. The controller 335 controls the reactant mixing valve through its output line 369'.

If the transient conversion is above the pre-coalescing transient conversion range, as earlier defined, the reactant mixing valve 369 is ordered by the controller 335 to increase the first content by increasing the ratio of the first reactant from line 370 to liquids from line 371. Similarly, if the transient conversion is under the "pre-coalescing transient conversion range", according to this invention, the reactant mixing valve 369 is ordered by the controller 335 to decrease the first content by decreasing the ratio of the first reactant from line 370 to liquids from line 371.

The change of first content is preferably conducted in increments, preferably in the range of 5 to 10% of the first content at the particular time.

After the transient conversion is found to be within the most desired range (20–60%, for example, in the case of cyclohexane to adipic acid, for example, under certain conditions), said transient conversion continues to be monitored with a goal in most cases to stay somewhere in the vicinity of the middle value of said most desired range (about 40%, for example). As in previous embodiments, continuous monitoring and control are highly preferable, since the conditions in the reaction chamber may vary, causing changes in the transient conversion values. Valves regulating ratios of liquids, and controlled by computerized controllers according to a desirable program are well known in the art.

Figure 5:
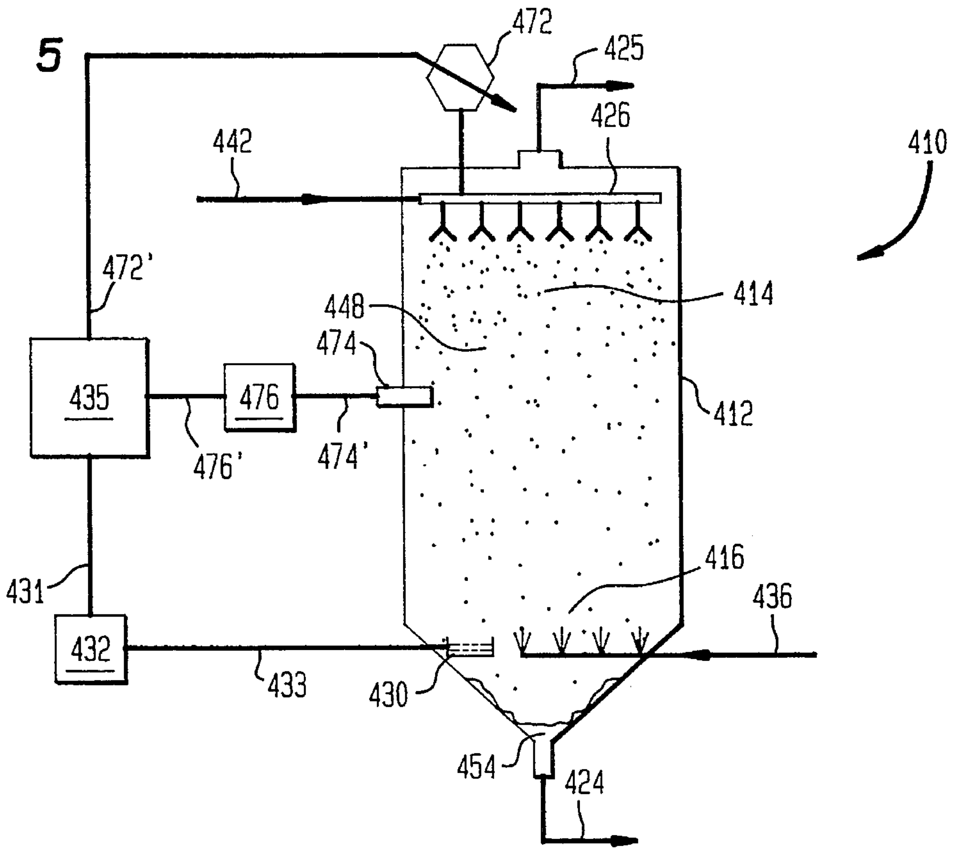
FIG. 5 illustrates schematically still another preferred embodiment of the present invention, wherein control of transient conversion is achieved by changing the droplet size or diameter.

In still another embodiment of the present invention, better shown in FIG. 5, the reaction chamber 412 is provided with an atomizer 426 in the vicinity of its upper end 414, and a sample collector 430 positioned in the vicinity of its lower end 416. The atomizer 426 may be operable by gas or preferably without the need of gas (usually referred to as "airless" in the art). The atomizer 426 of this embodiment is adapted to control at will the droplet size or diameter through a regulator 472. Such atomizers are well known in the art. For example, droplet diameter may change by changing the pressure of the liquid to be atomized, changing the orifice size, changing the frequency and/or intensity in the case of ultrasonic or other pulsation operated atomizers, changing the pressure of the gas in the case of gas operated atomizers, changing the rotation of the speed in the case of centrifugal atomizers, etc. For the purposes of the instant invention, the regulator 472 represents any mechanism well known to the art, which is adapted to controllably change any variable parameter of the atomizer which controls average diameter of the droplets.

The sample collector 430 is connected to the conversion monitor or detector 432 through sample line 433 for providing samples of droplets 448 trapped in the collector just (and coalesced, of course in the collector) before they coalesce onto the second liquid mass 454. The conversion monitor or detector 432 is connected, preferably electrically, to the controller 435 through input line 431 for transferring transient conversion information. In turn, the controller 435 is connected, preferably electrically, to the regulator 472 through output line 472' in order to control said regulator 472. For purposes of clarity, basically only the elements of the device 410, which illustrate this embodiment and its operation, are shown.

In operation of this embodiment, the first liquid containing the first reactant, cyclohexane for example, enters the reaction chamber 412 through line 442 in a manner that it is atomized by the atomizer 426, and forms a plurality of droplets 448.

At the same time that the first liquid is being atomized, a gas containing the oxidant, preferably oxygen in the case of cyclohexane, enters the chamber 412 through the gas inlet feed line 436, in the vicinity of the lower end 416 of the chamber 412. The gas, in addition to the oxidant, may also contain rather inert gases, such as nitrogen and/or carbon dioxide, for example. Off gases mixed with vapors of reactants, solvents, mist, and the like exit the reaction chamber 412 through outlet gas line 425 and are treated as it will exemplified at a later section.

As the droplets fall in a downwardly direction from the atomizer 426, they start reacting with the oxidant, which is oxygen for example. The second liquid 454 is removed, preferably continuously, through the liquid outlet line 424 as in the previous embodiments.

A part of the droplets 448 fall into the sample collector 430, from where, they are directed to the conversion detector or monitor 432, to be analyzed regarding transient conversion.

The information obtained in the conversion detector or monitor 432 is fed to computerized controller 435 through its input line 431, where it is processed by well known to the art techniques. The controller 435 controls the regulator 472 through its output line 472'.

If the transient conversion is above the pre-coalescing transient conversion range, as earlier defined, the regulator 472 is ordered by the controller 435 to increase the average diameter of the droplets. Similarly, if the transient conversion is under the "pre-coalescing transient conversion range", according to this invention, the regulator 472 is ordered by the controller 435 to decrease the average diameter of the droplets.

The change in droplet diameter is preferably conducted in increments, preferably in the range of 10 to 20% of the average droplet diameter at the particular time.

After the transient conversion is found to be within the most desired range (20–60%, for example, in the case of cyclohexane to adipic acid, for example, under certain conditions), said transient conversion continues to be monitored with a goal in most cases to stay somewhere in the vicinity of the middle value of said most desired range (about 40%, for example). As in previous embodiments, continuous monitoring and control are highly preferable, since the conditions in the reaction chamber may vary, causing changes in the transient conversion values. Valves regulating ratios of liquids, and controlled by computerized controllers according to a desirable program are well known in the art.

The device 410 may also optionally comprise an optical monitor 474, preferably of the fiber optic type, connected to an image analyzer 476 though line 474', which image analyzer is in turn connected to the computerized controller 435 through input line 476'. In operation of this arrangement, the image analyzer 476 determines the average droplet diameter from the image received from the optical monitor 474, and sends this information to the controller 435, which then incorporates said information to the rest of the processed data, so that it can be better control the average droplet diameter, by comparing for example the change ordered to regulator 472 with the droplet size change as a result of it.

Figure 6:
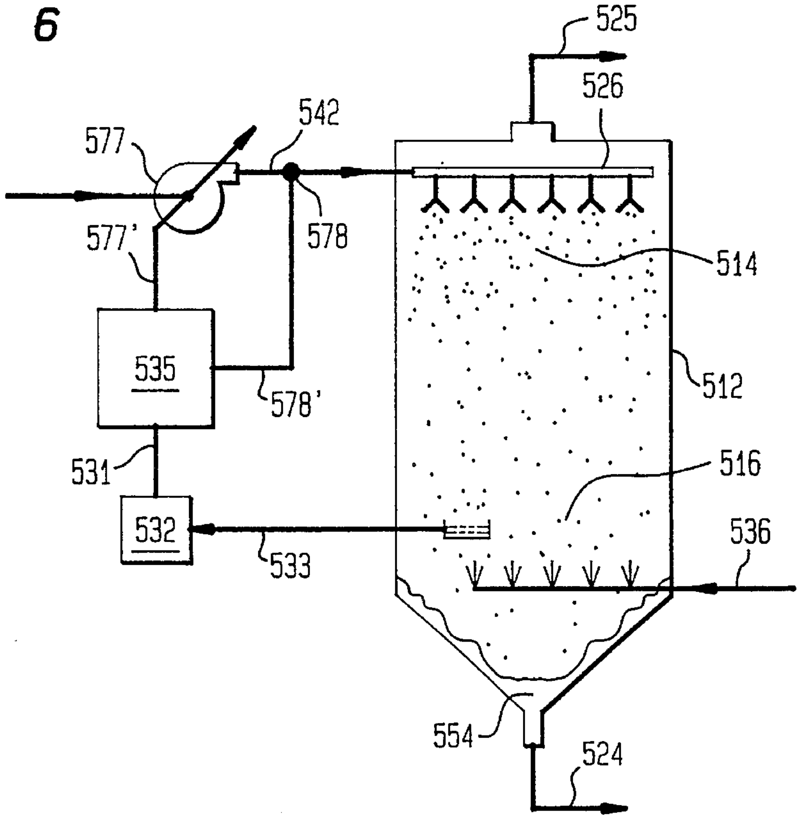
FIG. 6 illustrates schematically still another preferred embodiment of the present invention, wherein control of transient conversion is achieved by changing the first flow rate.

In a different embodiment of the present invention, better shown in FIG. 6, the reaction chamber 512 is provided with an atomizer 526 in the vicinity of its upper end 514, and a sample collector 530 positioned in the vicinity of its lower end 516. There is also provided a first liquid pump 577, which is adapted to regulate a first flow of the first liquid in line 542, and a flow meter 578 adapted to measure the rate of the first flow of the first liquid in line 542. The flow meter 578 is connected, preferably eclectically, to the computerized controller 535 through input line 578'. The sample collector 530 is connected to the conversion monitor or detector 532 through sample line 533 for providing samples of droplets 548 trapped in the collector just (and coalesced, of course in the collector) before they coalesce onto the second liquid mass 554. The conversion monitor or detector 532 is connected, preferably electrically, to the controller 535 through input line 531 for transferring transient conversion information. In turn, the controller 535 is connected, preferably electrically, to the first liquid pump 577 through output line 577' in order to control said first liquid pump 577. For purposes of clarity, basically only the elements of the device 510, which illustrate this embodiment and its operation, are shown.

In operation of this embodiment, the first liquid pump 577 pumps first liquid in line 542 at a desired first flow rate. Thus, the first liquid containing the first reactant, cyclohexane for example, in a first content, enters the reaction chamber 512 through line 542 in a manner that it is atomized by the atomizer 526 at a first flow rate, and forms a plurality of droplets 548.

At the same time that the first liquid is being atomized, a gas containing the oxidant, preferably oxygen in the case of cyclohexane, enters the chamber 512 through the gas inlet feed line 536, in the vicinity of the lower end 516 of the chamber 512. The gas, in addition to the oxidant, may also contain rather inert gases, such as nitrogen and/or carbon dioxide, for example. Off gases mixed with vapors of reactants, solvents, mist, and the like exit the reaction chamber 512 through outlet gas line 525 and are treated as it will exemplified at a later section.

As the droplets fall in a downwardly direction from the atomizer 526, they start reacting with the oxidant, which is oxygen for example. The second liquid 554 is removed, preferably continuously, through the liquid outlet line 524 as in the previous embodiments.

A part of the droplets 548 fall into the sample collector 530, from where, they are directed to the conversion detector or monitor 532, to be analyzed regarding transient conversion.

The information obtained in the conversion detector or monitor 532 is fed to computerized controller 535 through its input line 531, where it is processed by well known to the art techniques. Also, the flow rate measurement from the flow meter 578 is fed to the controller 535 and processed in coordination with the information from line 531. The controller 535 in turn controls the first liquid pump 577 through its output line 577', in a manner to increase or decrease the flow rate of first liquid in a programmed manner.

If the transient conversion is above the pre-coalescing transient conversion range, as earlier defined, the first liquid pump 577 is ordered by the controller 535 to increase the first flow rate, by increasing, for example, the pumping action. Similarly, if the transient conversion is under the pre-coalescing transient conversion range, as earlier defined, the first liquid pump 577 is ordered by the controller 535 to decrease the first flow rate, by decreasing, for example, the pumping action.

The change in first flow rate is preferably conducted in increments, preferably in the range of 5 to 10% of the first flow rate at the particular time.

After the transient conversion is found to be within the most desired range (20–60%, for example, in the case of cyclohexane to adipic acid, for example, under certain conditions), said transient conversion continues to be monitored with a goal in most cases to stay somewhere in the vicinity of the middle value of said most desired range (about 40%, for example). As in previous embodiments, continuous monitoring and control are highly preferable, since the conditions in the reaction chamber may vary, causing changes in the transient conversion values. Pumps regulating flow rate of liquids, and controlled by computerized controllers according to a desirable program are well known in the art.

Figure 7:
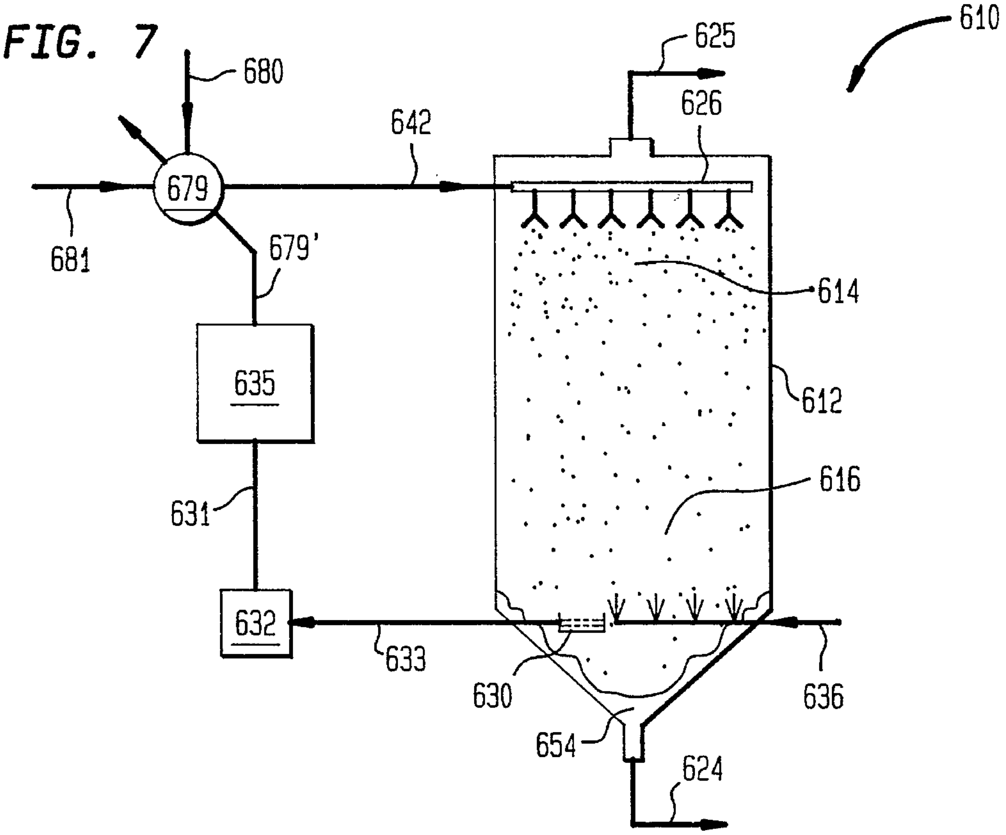
FIG. 7 illustrates schematically still another preferred embodiment of the present invention, wherein control of transient conversion is achieved by changing the volatilization rate.

In still a different embodiment of the present invention, better shown in FIG. 7, the reaction chamber 612 is provided with an atomizer 626 in the vicinity of its upper end 614, and a sample collector 630 positioned in the vicinity of its lower end 616. There is also provided a volatiles mixing valve 679, which is adapted to mix volatiles from line 680 and other liquids from line 681 in order to produce the first liquid in line 642. The sample collector 630 is connected to the conversion monitor or detector 632 through sample line 633 for providing samples of droplets 648 trapped in the collector just (and coalesced, of course in the collector) before they coalesce onto the second liquid mass 654. The conversion monitor or detector 632 is connected, preferably electrically, to the controller 635 through input line 631 for transferring transient conversion information. In turn, the controller 635 is connected, preferably electrically, to the volatiles mixing valve 679 through output line 679' in order to control said volatiles mixing valve 679. For purposes of clarity, basically only the elements of the device 610, which illustrate this embodiment and its operation, are shown.

In operation of this embodiment, volatiles from line 680 and other liquids from line 681 are mixed in proportions regulated by the volatiles mixing valve 679, in order to produce the first liquid in line 642 so that said first liquid has a desired content of volatiles. The volatiles are substances, of usually lower boiling point than that of the first reactant, which under the conditions of the reaction have a tendency to volatilize as the first liquid is atomized in the reaction chamber and lower conversion rates. The volatiles have preferably low or no reactivity under the reaction conditions. In the case of oxidation of cyclohexane to adipic acid, acetic acid and/or acetone, for example, would represent volatiles.

The liquids from line 681 contain first reactant, along with solvents, catalysts, promoters, initiators, recycled ingredients, and the like. The first liquid containing the first reactant, cyclohexane for example, enters the reaction chamber 612 through line 642 in a manner that it is atomized by the atomizer 626, and forms a plurality of droplets 648.

At the same time that the first liquid is being atomized, a gas containing the oxidant, preferably oxygen in the case of cyclohexane for example, enters the chamber 612 through the gas inlet feed line 636, in the vicinity of the lower end 616 of the chamber 612. The gas, in addition to the oxidant, may also contain rather inert gases, such as nitrogen and/or carbon dioxide, for example. Off gases mixed with vapors of reactants, solvents, mist, and the like exit the reaction chamber 612 through outlet gas line 625 and are treated as it will exemplified at a later section.

As the droplets fall in a downwardly direction from the atomizer 626, they start reacting with the oxidant, which is oxygen for example. The second liquid 654 is removed, preferably continuously, through the liquid outlet line 624 as in the previous embodiments.

A part of the droplets 648 fall into the sample collector 630, from where, they are directed to the conversion detector or monitor 632, to be analyzed regarding transient conversion.

The information obtained in the conversion detector or monitor 632 is fed to computerized controller 635 through its input line 631, where it is processed by well known to the art techniques. The controller 635 controls the volatiles mixing valve 679 through its output line 679'.

If the transient conversion is above the pre-coalescing transient conversion range, as earlier defined, the volatiles mixing valve 679 is ordered by the controller 635 to increase the introduction of volatiles from obtained from line 680. Similarly, if the transient conversion is under the "pre-coalescing transient conversion range", according to this invention, the volatiles mixing valve 679 is ordered by the controller 635 to decrease or eliminate the introduction of volatiles from line 680.

The increase or decrease of volatiles is preferably conducted in increments, preferably in the range of 2 to 5% based on the total weight of the first liquid at that particular time.

After the transient conversion is found to be within the most desired range (20–60%, for example, in the case of cyclohexane to adipic acid, for example, under certain conditions), said transient conversion continues to be monitored with a goal in most cases to stay somewhere in the vicinity of the middle value of said most desired range (about 40%, for example). As in previous embodiments, continuous monitoring and control are highly preferable, since the conditions in the reaction chamber may vary, causing changes in the transient conversion values. Valves regulating ratios of liquids, and controlled by computerized controllers according to a desirable program are well known in the art.

If the liquids in line 681 are arranged to contain no or only small amounts of catalyst, then catalyst may be added through line 680 at a desired base level. Addition of higher amounts of catalyst will favor increase of transient conversion, while addition of lower amounts of catalyst will favor decrease of of transient conversion.

The increase or decrease of catalyst level is preferably conducted in increments, preferably in the range of 5 to 10% based on the total weight of the catalyst contained in the first liquid at that particular time.

Figure 8:
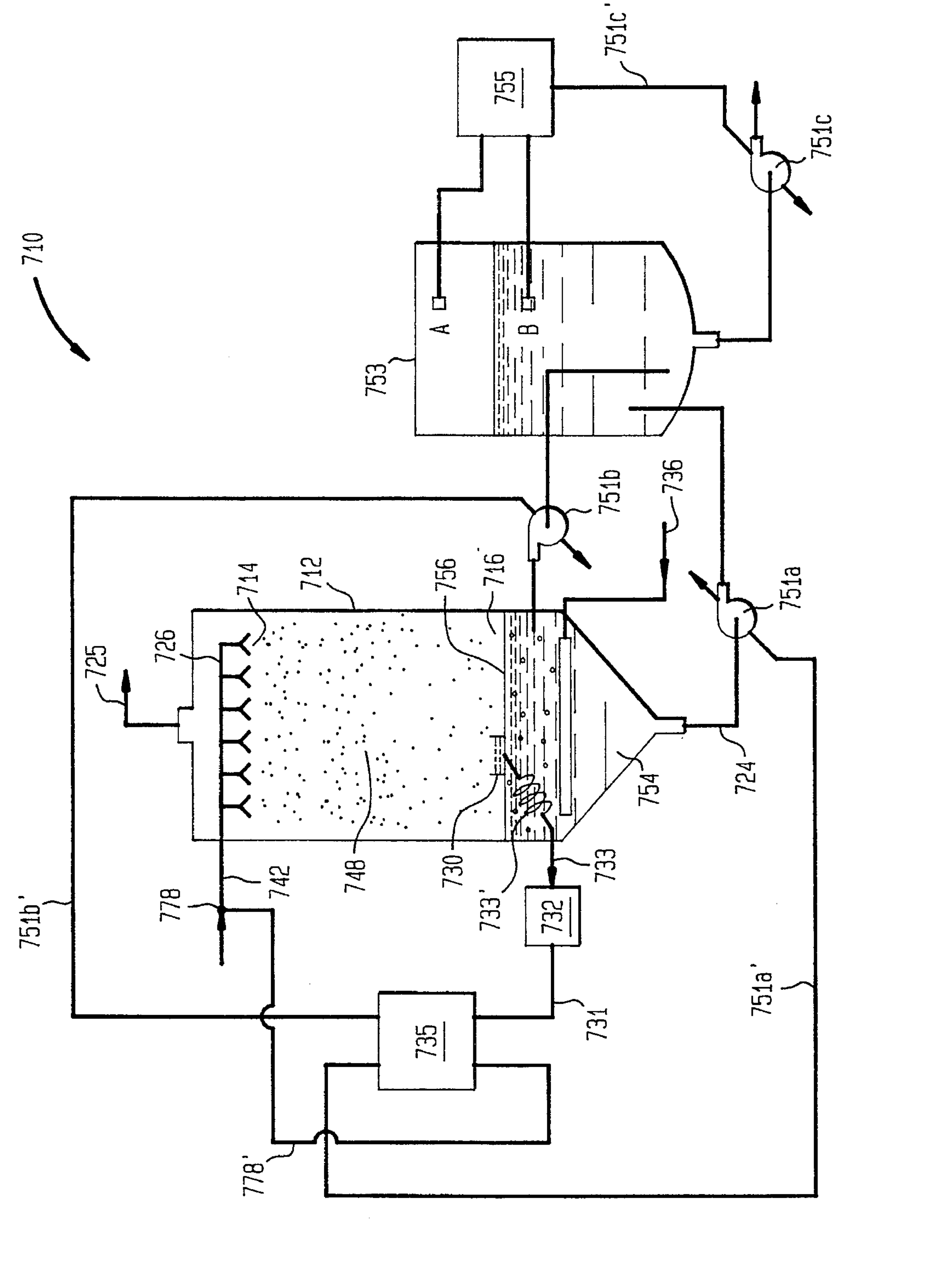
FIG. 8 illustrates schematically still another preferred embodiment of the present invention, wherein control of transient conversion is achieved by changing the atomization distance through moving the level of the surface of the second liquid

In still another embodiment, better shown in FIG. 8, the reaction chamber 712 is provided with an atomizer 726 in the vicinity of its upper end 714, and a sample collector 730 adapted to be floating as a boat on liquid 754 at the lower end 716 of the reaction chamber 712. The atomizer 726 is provided with first liquid from line 742, which contains a flow meter 778. There is also provided a retaining tank 753, connected to the vicinity of the lower end 716 of the reaction chamber 712 through two pumps 751 a and 751*b*. The retaining tank 753 is also connected to pump 751*c*, which is adapted to transfer liquid to a separator (shown as 15 in FIG. 1). There is further provided a level controller 755, which controls pump 751*c*, based on the level of liquid in retaining tank 753, by well known to the art techniques. The level controller activates pump 751*c* through output line 751*c*' when the liquid exceeds level A, and deactivates said pump 751*c* when the liquid goes lower than level B.

Figure 9:
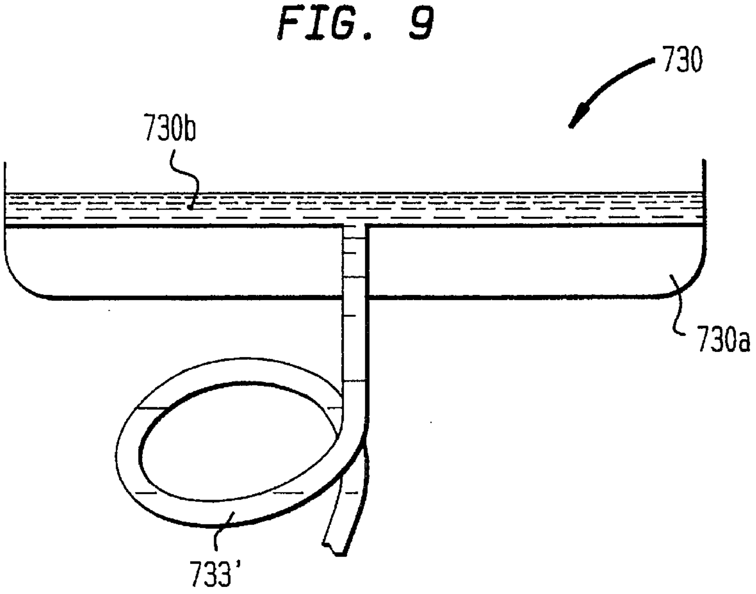
FIG. 9 illustrates schematically the sample collector utilized in the embodiment of FIG. 8.

The sample collector 730 is connected to the conversion monitor or detector 732 through sample line 733, which has a flexible coiled portion 733' for providing samples of droplets 748 trapped in the collector just (and coalesced, of course in the collector) before they coalesce onto the second liquid mass 754. The sample collector 730 has a boat like configuration provided with a closed float portion 730*a*, and a sample portion 730*b*, as better shown in FIG. 9. The flexible coiled portion 733' of line 733 allows the boat-like sample collector 730 to move freely along with the surface 756 of the second liquid mass 754.

The conversion monitor or detector 732 is connected, preferably electrically, to the controller 735 through input line 731 for transferring transient conversion information. Also the flow meter 778 is connected, preferably electrically, to the controller 735 through input line 778' for transferring flow rate information regarding the first liquid entering the reaction chamber 712 through the atomizer 726. In turn, the controller 735 is connected, preferably electrically, to pumps 751*a* and 751*b* through output lines 751*a*' and 751*b*, respectively, for controlling said pumps 751*a* and 751*b*.

For purposes of clarity, basically only the elements of the device 710, which illustrate this embodiment and its operation, are shown.

In operation of this embodiment, the first liquid containing the first reactant, cyclohexane for example, enters the reaction chamber 712 through line 742 in a manner that it is atomized by the atomizer 726, and forms a plurality of droplets 748.

At the same time that the first liquid is being atomized, a gas containing the oxidant, preferably oxygen in the case of cyclohexane for example, enters the chamber 712 through the gas inlet feed line 736, in the vicinity of the lower end 716 of the chamber 712. The gas, in addition to the oxidant, may also contain rather inert gases, such as nitrogen and/or carbon dioxide, for example. Off gases mixed with vapors of reactants, solvents, mist, and the like exit the reaction chamber 712 through outlet gas line 725 and are treated as it will exemplified at a later section.

As the droplets fall in a downwardly direction from the atomizer 726, they start reacting with the oxidant, which is oxygen for example. The second liquid 754 may be removed through the liquid outlet line 724 with pump 751*a*.

A part of the droplets 748 fall into the sample collector 730, from where, they are directed through line 733 and its flexible portion 733' to the conversion detector or monitor 732, to be analyzed regarding transient conversion.

The information obtained in the conversion detector or monitor 732 is fed to computerized controller 735 through its input line 731, where it is processed by well known to the art techniques. The controller 735 controls pumps 751*a* and 751*b*, as aforementioned.

If the transient conversion is above the pre-coalescing transient conversion range, as earlier defined, pump 751*a* is ordered by the controller 735 to stop its pumping action, and pump 751*b* is activated. This causes the surface 756 of the second liquid mass 754 to rise, resulting in smaller atomization distance, as defined earlier. In turn, smaller atomization distance causes the transient conversion to decrease. Similarly, if the transient conversion is under the pre-coalescing transient conversion range, as earlier defined, pump 751*a* is ordered by the controller 735 to start or continue its pumping action, and pump 751*b* is deactivated. This causes the surface 756 of the second liquid mass 754 to drop, resulting in higher atomization distance. In turn, higher atomization distance causes the transient conversion to increase.

The level 756 of the second liquid mass 754 may be determined by the controller 735 either indirectly by correlating the amounts of incoming first liquid (through the atomizer, as measured by the flow meter 778 and obtained by the controller 735 through line 778', and through pump 751*b*) and outcoming second liquid 754 through pump 751*a* , or directly by use of a level measuring device (not shown for purposes of clarity) in the reaction chamber. Level measuring devices are well known in the art.

The level of liquids in the retaining tank 753 is controlled by level controller 755. When the level goes under level B, pump 751*c* is deactivated by the controller 755. If the liquid level exceeds level A, pump 751*c* is activated again by controller 755. The retaining pump 753 should contain enough liquid at its lowest level B to take care of any given variations of liquid level 756 in the reaction chamber 712.

The increase or decrease of atomization distance is preferably conducted in increments, preferably in the range of 2 to 5% of the atomization distance at the time the measurement is made.

After the transient conversion is found to be within the most desired range (20–60%, for example, in the case of cyclohexane to adipic acid, for example, under certain conditions), said transient conversion continues to be monitored with a goal in most cases to stay somewhere in the vicinity of the middle value of said most desired range (about 40%, for example). As in previous embodiments, continuous monitoring and control are highly preferable, since the conditions in the reaction chamber may vary, causing changes in the transient conversion values. Valves regulating ratios of liquids, and controlled by computerized controllers according to a desirable program are well known in the art.

Going back to FIG. 1, the separator 15, as aforementioned, can be any assembly of equipment, simple or complicated, which is capable of separating the intermediate oxidation product from the second liquid. Such equipment is well known to the art, as described for example in a plethora of patents regarding separation of adipic acid from the mother liquor (second liquid in this case).

Figure 10:
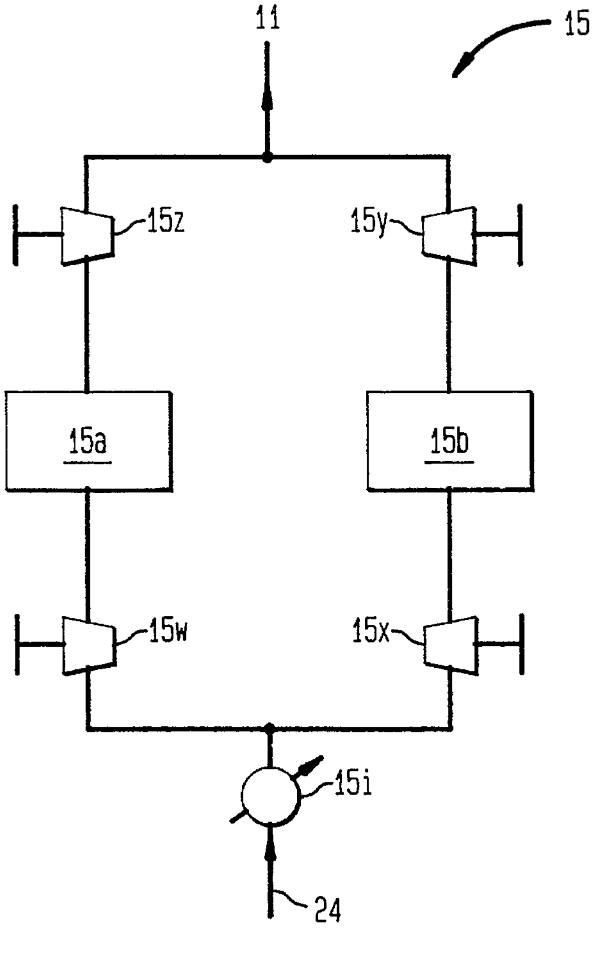
FIG. 10 illustrates schematically a filter arrangement comprised in the separator according to another preferred embodiment of the present invention.

In the case that the oxidation product is a solid having limited solubility in the second liquid, either at the reaction temperature or any other temperature, as is the case of adipic acid in the case of its production from oxidation of cyclohexane, the separator 15 may comprise, according to this invention, two filters 15a and 15b connected in parallel, as better shown in FIG. 10. The separator 15 may also comprise valves 15*w*, 15*x*, 15*y*, and 15*z*, as well as an optional heat removal device 15*i*, which may take the form of a crystallizer.

In operation of this separator, valves 15*x* and 15*y* are initially open, while valves 15*w* and 15*z* are closed. While valves 15*w* and 15*z* are closed, any solid oxidation product previously accumulated in filter 15*a*, such as adipic acid for example, is separated from said filter 15*a*, either manually or automatically (back-flush, scraping, and the like well known to the art, for example/not shown). Second liquid from line 24, optionally passing through heat removal device 15i for changing the liquid temperature to a more appropriate temperature for the solid separation, passes through filter 15*b*, where the solid oxidation product is removed from the second liquid, which second liquid follows line 11 for recirculation to the recirculation tank 19 (FIG. 1 ) or further processing in other equipment (not shown). When filter 15*a* has been substantially emptied, and filter 15*b* has been substantially full or otherwise ready for being emptied, valves 15*w* and 15*z* are opened and valves 15*x* and 15*y* are closed, so that filtering of solid oxidation product takes place now in filter 15*a*, while filter 15*b* is being emptied. This cycle is repeated in the process. Of course, alternate devices may be used, such as for example, rotary drum filters and the like.

In a different embodiment of this invention, better shown in FIG. 11, the apparatus or device 810 of the present invention, also comprises a condenser 857 connected to the gas outlet 823 through line 825, and to condensate tank 859, which serves as a reservoir of condensate collected from condenser 857. The condensate tank 859, through valve 865 is connected to line 865', which in turn is connected to the liquid dispensing ring 844, or it is connected to line 865", which in turn leads to line 811 for recycling the condensed liquids to the recycling tank 819. The valve 865 is adapted to direct the condensed liquids totally to line 865', or totally to line 865", or partially to line 865' and partially to line 865", or be closed and not permit any transfer of condensed liquids.

The device 810 also comprises a heat exchanger 838 connected to the recycling tank 819; an eductor or aspirator 861, connected to the heat exchanger 838; a pump 877 connected to the eductor 861 at the intake and to the atomizer 826 at the other end. The eductor 861 is adapted to produce vacuum to line 867' through regulating valve 867 (when the regulating valve 867 is in an open position) and through check valve 867a, which allows flow from line 867' toward the pump but not vice versa. Line 867' is connected to line 857' between the condenser 857 and the valve 864. An additional pump (not shown) may be placed between the eductor 861 and the heat exchanger 838, which in coordination with pump 877 may control the vacuum produced by the eductor 861 toward line 867'. It may be also utilized to prevent starvation of pump 877 from first liquid. The heat exchanger 838 may be part of the condenser 857 (not shown as such in FIG. 11 ), so that heat received from condensibles is used as heat source for the heat exchanger 838.

Lines 841*a*, 841*b*, and 841*c* are used to supply the recirculation tank with appropriate amounts of raw materials, catalysts, solvents, initiators, promoters and the like.

In operation of this embodiment, first liquid from the recycling tank is heated to the desired temperature in heat exchanger 838. The heated first liquid is pumped through pump 877 to the atomizer 826, where it is broken into droplets 848, which finally coalesce onto the second liquid 854 as already discussed in previous embodiments. At the same time, gas containing an oxidant, preferably oxygen, enters the reaction chamber 812 in a counterflow direction with regard to the droplets, as also discussed earlier, and the oxidant reacts with the first reactant contained in the droplets of the first liquid. Any off-gases produced during the reaction, which are usually non-condensible unless subjected to extremely low temperatures, along with condensibles leave the reaction chamber 812 through gas outlet 823. Following line 825, they enter the condenser 857, where the condensibles condense to condensate, which condensate is accumulated into the condensate tank 859.

If it is desired to form a curtain or thick film 845, the condensate is directed, at least partially, through valve 865 to line 865', from where it is fed to the liquid dispensing ring 844 and forms said curtain 845, useful to prevent sticking of any reaction or other solid products to the walls of the reactor 812. This condensate has the advantage over the recycled liquid coming through line 11' of FIG. 1, for example, that in most cases it is substantially catalyst free. This is because in the practice of this invention, non volatile catalysts, such as metal salts for example, are utilized in most occasions.

If no condensate is needed to supply the liquid dispensing ring, the 865 is caused to direct the condensate to line 865", which feeds it to line 811, so that the condensate is finally transferred to the recirculation tank 819. In general, as aforementioned, the valve 865 is adapted to direct the condensed liquids totally to line 865', or totally to line 865", or partially to line 865' and partially to line 865", or be closed and not permit any transfer of condensed liquids.

The non-condensible gases follow line 857', and exit the system through valve 864, if so desired. Valve 864, as also shown in other embodiments, is preferably controllable to open and close to any degree demanded by the operation. If it is desired to remove all non-condensible gases from the system, valve 864 is opened to a desired degree for the pressure inside the system to be maintained to desired levels, and valve 867 is completely closed. If it is desired to only partially remove non-condensibles, both valves 864 and 867 are opened to the desired degree, so that vacuum formed by the eductor or aspirator 861, recirculates the part of non-condensibles caused by the vacuum to enter the reaction chamber 812. Complete recirculation of non-condensibles without any non-condensibles leaving the system is only possible if no new flow of gas containing oxidant takes place after a certain point, so that the pressure inside the reaction chamber 812 will not finally exceed predetermined limits. Check valve **867*a* does not hinder the flow of non-condensibles, but it prevents entry of first liquid to line 867' in case of accidental flooding of the aspirator 861**.

Figure 12:
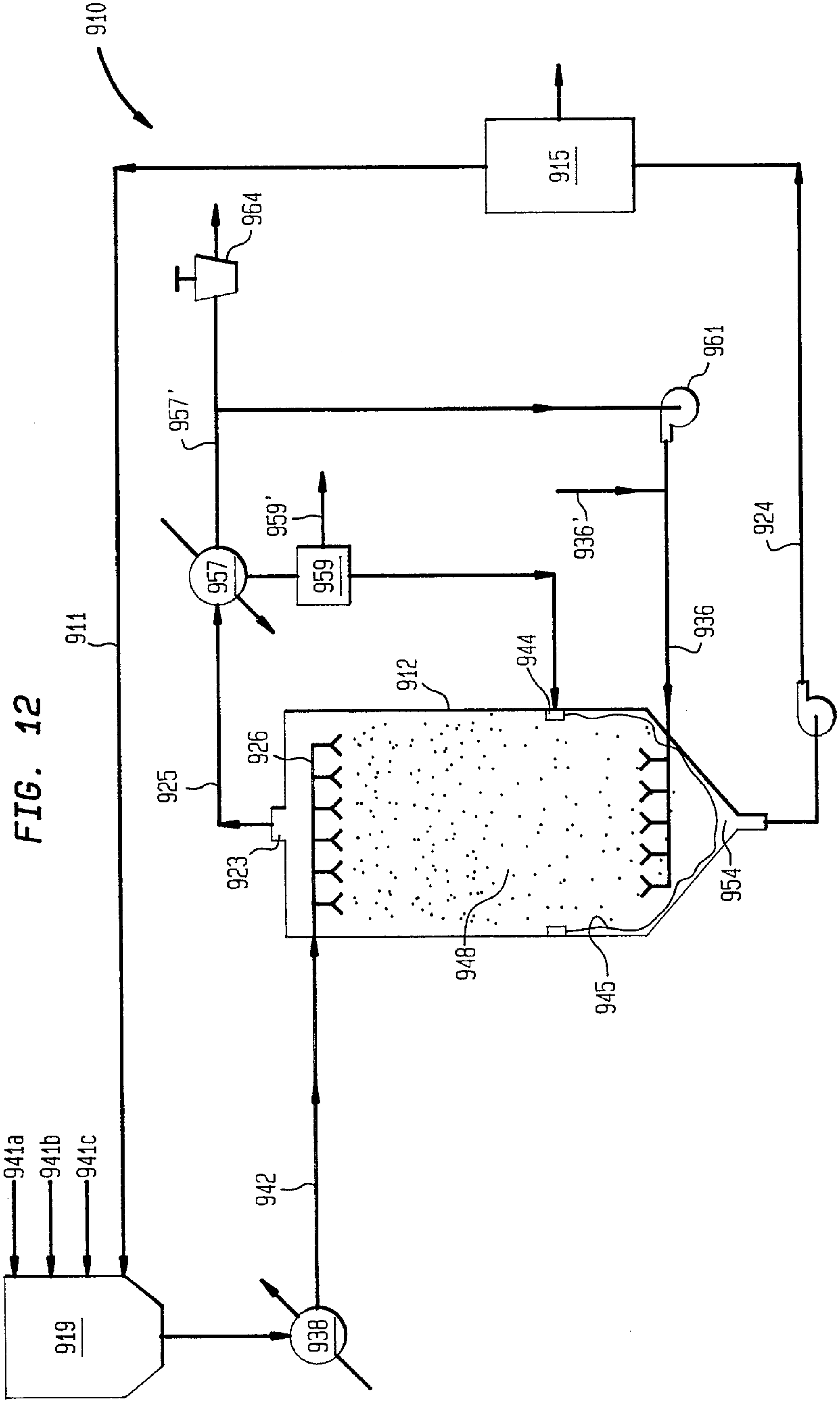
FIG. 12 illustrates schematically still another preferred embodiment of the present invention, wherein a pump is utilized to recirculate non-condensible off-gases, a condenser is used to condense condensibles, and part of the condensibles return to the reaction chamber, where a thick film or curtain is formed for preventing solids buildup on the walls.

In still a different embodiment of this invention, better shown in FIG. 12, the apparatus or device 910 of the present invention, also comprises a condenser 957 connected to the gas outlet 923 through line 925, and to condensate tank 959, which serves as a reservoir of condensate collected from condenser 957. The condensate tank 959, is connected to the liquid dispensing ring 944. The condenser 957 is also connected to a valve 964 through line 957', which valve is adapted to release non-condensibles, if in an open position.

The device 910 also comprises a heat exchanger 938 connected to the recycling tank 919 and to the atomizer 926 at the other end. It also comprises a gas pump 961 connected to line 957' through line 967' adapted to transfer non-condensibles from line 957' to the gas inlet feed line 936. A replenish gas line 936' is also connected to line 936 for providing fresh gas containing oxidant, preferably oxygen.

The heat exchanger 938 may be part of the condenser 957 (not shown as such in FIG. 11 ), so that heat received from condensibles is used as heat source for the heat exchanger 938.

Lines **941*a*, 941*b*, and 941*c*** are used to supply the recirculation tank with appropriate amounts of raw materials, catalysts, solvents, initiators, promoters and the like.

In operation of this embodiment, first liquid from the recycling tank is heated to the desired temperature in heat exchanger 938, and enters the atomizer 926, where it is broken into droplets 948, which finally coalesce onto the second liquid 954 as already discussed in previous embodiments. At the same time, gas containing oxidant, preferably oxygen, enters the reaction chamber 912 through line 936 in a counterflow direction with regard to the droplets, as also discussed earlier, and the oxidant reacts with the first reactant contained in the droplets of the first liquid. Any off-gases produced during the reaction, which are usually non-condensible unless subjected to extremely low temperatures, along with condensibles leave the reaction chamber 912 through gas outlet 923. Following line 925, they enter the condenser 957, where the condensibles condense to a condensate, which condensate is accumulated into the condensate tank 959.

The condensate is directed, at least partially as discussed in other embodiments, to the liquid dispensing ring 944 and forms curtain 945, useful to prevent sticking of any reaction or other solid products to the walls of the reactor 912. This condensate has the advantage over the recycled liquid coming through line 11' of FIG. 1, for example, that in most cases it is substantially catalyst free. This is because in the practice of this invention, non volatile catalysts, such as metal salts for example, are utilized in most occasions.

If no condensate is needed to supply the liquid dispensing ring 944, the condensate may be directed elsewhere through line 959'.

The non-condensible gases follow line 957', and exit the system through valve 964, if so desired. Valve 964, as also shown in other embodiments, is preferably controllable to open and close to any degree demanded by the operation. If it is desired to remove all non-condensible gases from the system, valve 964 is opened to a desired degree for the pressure inside the system to be maintained to desired levels, and pump 961 is deactivated. If it is desired to have only partial removal of non-condensibles, valve 964 is opened to the desired degree, and pump 961 is also activated to the desired degree so that this combination causes recirculation of part of non-condensibles to the reaction chamber 912. Complete recirculation of non-condensibles without substantially any non-condensibles leaving the system may be preferably conducted by not allowing new flow of inert gas diluents to take place after a certain point, so that the pressure inside the reaction chamber 912 does not finally exceed predetermined limits.

The second liquid 954 is directed to the separator 915, through line 924, where the intermediate oxidation product is separated and the remaining liquids are either sent to another separator (not shown) for further separation of constituents, or they are directed to the recycling tank 919 for recycling, or a combination thereof.

Figure 13:
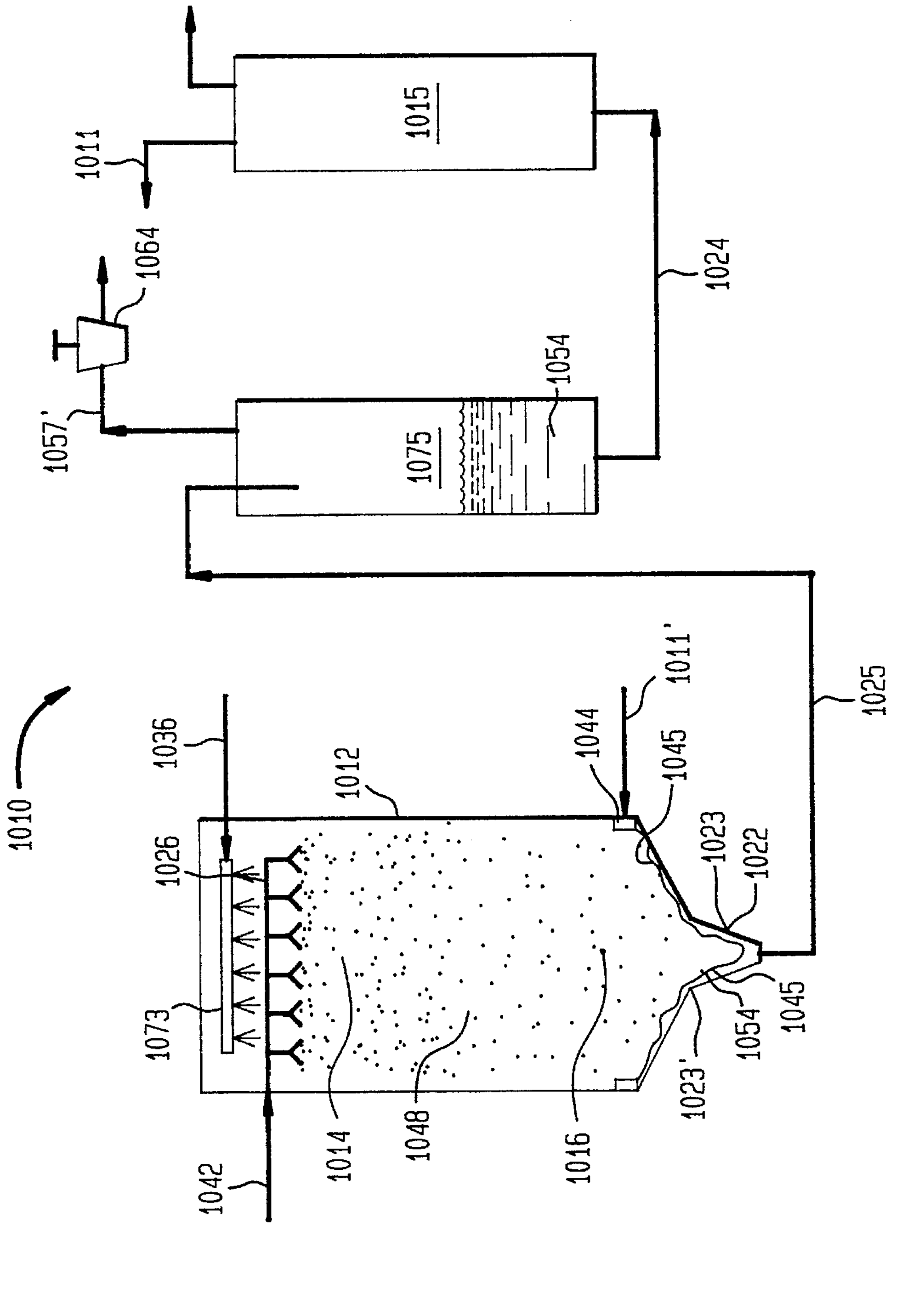
FIG. 13 illustrates schematically still another preferred embodiment of the present invention, wherein both condensibles and non-condensibles leave the reactor through the lower end.

In another embodiment of this invention, better shown in FIG. 13, the reaction chamber 1012 has a gas outlet 1023, which coincides with the liquid outlet 1022, preferably in the vicinity of the lower end 1016 of the reaction chamber 1012. Both the gas distributor 1073 fed by gas inlet line 1036, and the atomizer 1026 fed by line 1042, are preferably disposed at the upper end 1014 of the reaction chamber 1012. The gas distributor 1073 and the atomizer 1026 may be combined into one unit, and the gas may be used to help or totally be responsible for the atomization process.

The liquid/gas output 1022/1023 has preferably a conical shape of reduced diameter as compared to the diameter of the reaction chamber 1012, as illustrated in FIG. 13. The liquid dispensing ring 1044 is preferably positioned either at the bottom of the reaction chamber as shown in FIG. 13, or at the top 1023' of the liquid/gas output 1022/1023. Preferably, the liquid dispensing ring 1044 is adapted to deliver the liquids in a swirling manner. A cooler (not shown) may be placed in line 1011' in order to cool the liquids to a desired temperature adequate to condense condensibles exiting from the reaction chamber 1012 through the liquid/gas output 1022/1023.

There is also provided a liquid/gas separator 1075 for receiving the condensed condensibles and the non-condensibles from the reaction chamber 1012 through line 1025 and separating the second liquid 1054 from the non-condensibles. The liquid/gas separator 1075 is in turn connected to separator 1015, which is adapted to separate the intermediate oxidation product from the reactants and other materials introduced into the system in the process.

In operation of this embodiment, first liquid is introduced to the atomizer 1026 through line 1042, where it is broken into droplets 1048, which finally coalesces in the vicinity of the lower end 1016, preferably on the curtain or thick film 1045 and within the liquid/gas output 1022/1023. At the same time, gas containing an oxidant, preferably oxygen, enters the reaction chamber 1012 in the same direction with regard to movement of the droplets, and the oxidant reacts with the first reactant contained in the droplets of the first liquid as both droplets and gas travel in a direction from the upper end 1014 to the lower end 1016 of the reaction chamber 1012. Condensibles condense on the swirling cold liquids entering the system through line 1011'. The liquids coming in the reaction chamber through line 1011' may be derived from within the system or from outside the system. Any off-gases produced during the reaction, which are usually non-condensible unless subjected to low temperatures, along with condensibles leave the reaction chamber 1012 through the liquid/gas output 1022/1023. Following line 1025, they enter the liquid/gas separator 1075, where the second liquid 1054 is separated from the non-condensibles, which are removed through line 1057' and valve 1064, which valve may operate as already discussed in previous embodiments.

The second liquid 1054 is directed to the separator 1015, where it is treated as already discussed in previous embodiments.

As mentioned earlier, condensation of condensibles may be inside the pressurized device, such as for example device 810 and 910 of FIGS. 11 and 12, respectively, in the respective condensers 857 and 957, before the respective valves 864 and 964, which are used to purge the non condensibles, such as miscellaneous off-gases, which may include one or more of oxygen, nitrogen, carbon monoxide, carbon dioxide, and the like, for example. This particular type of condensation, albeit outside the reaction chamber, is by definition internal condensation, according to this invention, and it takes place at a pressure which is substantially the same as the reaction pressure.

According to this invention, internal condensation inside the reactor may also take place, and in many occasions it is preferable to the outside internal condensation. Internal condensation (before substantial pressure drop) is highly preferable to external condensation (after substantial or total pressure drop). Internal inside condensation is especially suitable in the case of employing close to stoichiometric amounts of oxidant for the oxidation process.

Figure 14:
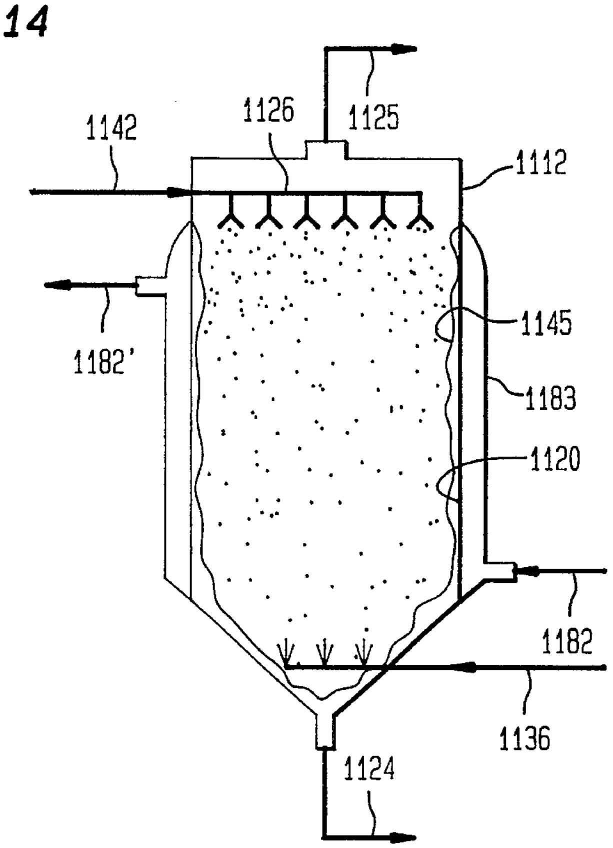
FIG. 14 illustrates schematically still another preferred embodiment of the present invention, wherein a cooling mantle surrounds the reaction chamber.

One embodiment of the instant invention utilizing internal inside condensation is better shown in FIG. 14, wherein only a limited number of elements is shown, for purposes of clarity. There is provided a cooling mantle 1183 surrounding the reaction chamber 1112 in all or part of its height. Otherwise, the reaction chamber 1112 comprises the same elements as in the previous embodiments.

The operation of this embodiment is similar to the operation of the previous embodiments with the exception that a cooler enters the mantle 1183 through line 1182 and exits through line 1182'. The temperature of the cooler is such as to cool down the wall 1120 adequately for vapors of condensibles inside the reaction chamber to condense and form a thick film or curtain 1145. Since the catalyst (metal salt for example, such as cobalt acetate, for example) in most cases is not volatile, it does not transfer to this curtain. Further, the temperature of the thick film is lower than that of the temperature of the droplets. Thus, no substantial reaction takes place within the curtain, and in addition to other advantages, the thick film or curtain 1145 prevents solid buildup on the walls of the condenser.

Figure 15:
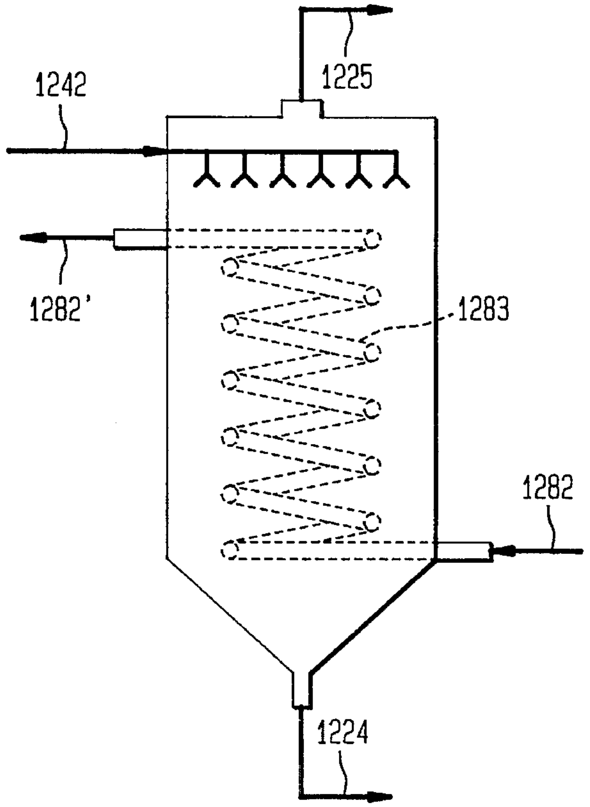
FIG. 15 illustrates schematically still another preferred embodiment of the present invention, wherein a cooling coil performs condensation inside the reaction chamber.

Another embodiment of the instant invention utilizing internal inside condensation is better shown in FIG. 15, wherein only a limited number of elements is shown, for purposes of clarity. There is provided a cooling coil 1283 inside the reaction chamber 1212, having an entry coolant line 1282 and a coolant exit line 1282'. The coil may be extending through the whole height of the reactor or just through part of it. The coil 1283 may be positioned vertical as shown in FIG. 15, or horizontal, or it may have any other suitable for the circumstances direction. Otherwise, the reaction chamber 1212 comprises the same elements as in the previous embodiments.

The operation of this embodiment is similar to the operation of the previous embodiments with the exception that a cooler enters the coil 1283 through line 1282 and exits through line 1282'. The temperature of the cooler is such as to cool down the coil 1283 adequately for vapors of condensibles inside the reaction chamber to condense on said coil 1283. Since the catalyst (metal salt for example, such as cobalt acetate, for example) in most cases is not volatile, it does not transfer to the condensate on the coil. Further, the temperature of the condensate on the coil 1283 is lower than that of the temperature of the droplets. Thus, reactants and catalysts contained in droplets coalescing on the coil are considerably diluted, and no substantial reaction takes place within a thick film (not shown) formed on the coil from condensate and coalesced droplets. The thick film also prevents solid buildup on the coil.

Figure 16:
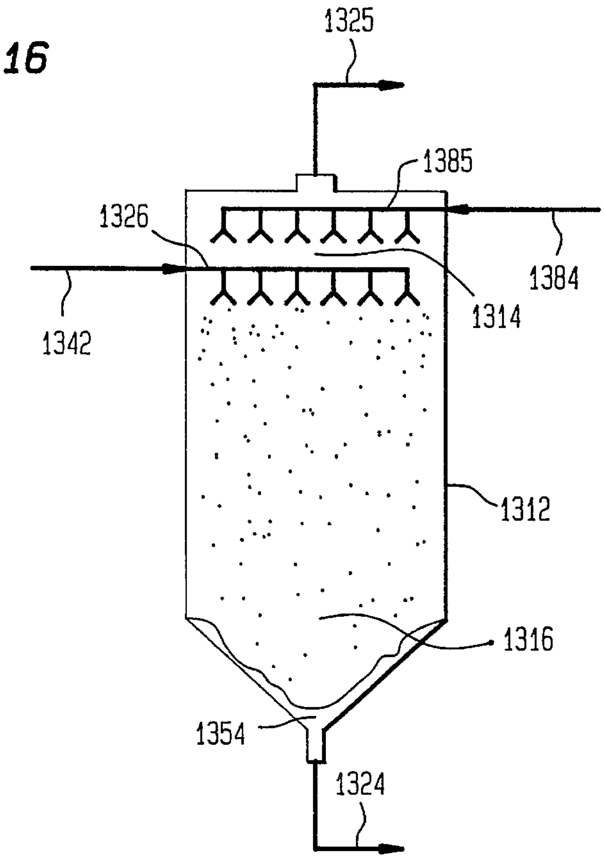
FIG. 16 illustrates schematically still another preferred embodiment of the present invention, wherein condensation is performed by spraying a cooling liquid along with atomization of the first liquid.

Still another embodiment of the instant invention utilizing internal inside condensation is better shown in FIG. 16, wherein only a limited number of elements is shown, for purposes of clarity. There is provided a cooling liquid sprayer 1385, preferably at the upper end 1314 of the reaction chamber 1312, and even more preferably disposed on top of the atomizer 1326, having an entry cooling liquid line 1384. Otherwise, the reaction chamber 1312 comprises the same elements as in the previous embodiments.

The operation of this embodiment is similar to the operation of the previous embodiments with the exception that a cooling liquid enters the cooling liquid sprayer 1385 through line 1384. It is then atomized by sprayer 1385. The cooling liquid comprises preferably either the same solvent contained in the first liquid or first reactant contained in the first liquid. For example, in the case of preparation of adipic acid from cyclohexane, the cooling liquid preferably comprises acetic acid (solvent), or cyclohexane (first reactant), or a mixture thereof. Preferably, no catalyst is contained in the cooling liquid. The temperature at which the cooling liquid is atomized is such that condensibles condense on the droplets of the atomized cooling liquid, thus providing internal inside condensation. As aforementioned, the droplets of the first liquid do not mix with the cooling liquid droplets, for all practical purposes, while both are being suspended in the gas, so that oxidation proceeds unhindered within the droplets of the first liquid. Finally, both types of droplets coalesce together at the lower end 1316 of the reaction chamber 1312 to form the second liquid 1353, which is removed through line 1324 for further treatment, as described in previous embodiments. In determination of the transient conversion, the flow rate of the cooling liquid and the flow rate of the first liquid have to be taken into account by well known to the art techniques in the controller (for example shown as 35 in FIG. 1).

Figure 17:
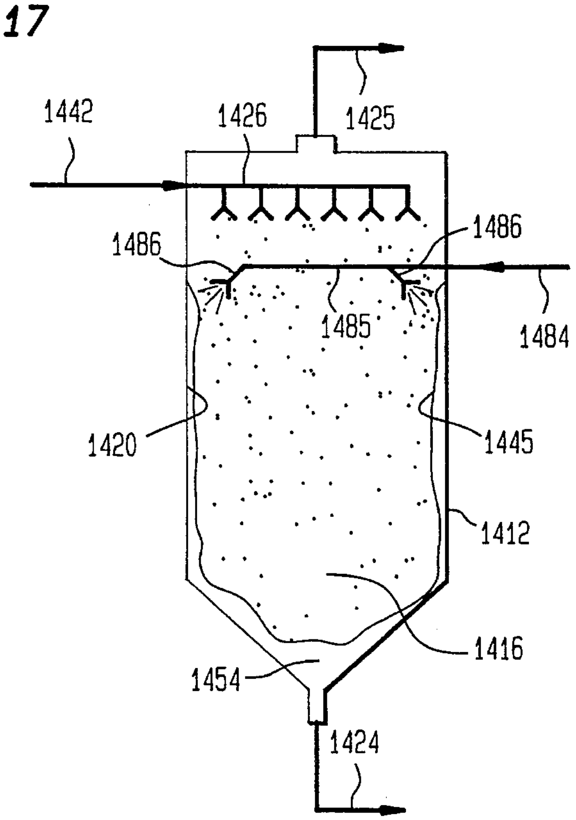
FIG. 17 illustrates schematically still another preferred embodiment of the present invention, wherein condensation is performed by sprayed a cooling liquid towards the walls of the reaction chamber.

A different embodiment of the instant invention utilizing internal inside condensation is better shown in FIG. 17, wherein only a limited number of elements is shown, for purposes of clarity. There is provided a cooling liquid sprayer 1485, preferably at the upper end 1414 of the reaction chamber 1412 having an entry cooling liquid line 1484. The sprayer 1485 has preferably a plurality of spray nozzles 1486 around its perimeter. The spray nozzles 1486 are directed toward the wall 1420 of the reaction chamber 1412. Otherwise, the reaction chamber 1412 comprises the same elements as in the previous embodiments.

The operation of this embodiment is similar to the operation of the previous embodiments with the exception that a cooling liquid enters the cooling liquid sprayer 1485 through line 1484. It is then atomized by sprayer 1485 through nozzles 1486, and falls on the walls 1420 of the reaction chamber 1412, where it forms a thick film or curtain 1445. The cooling liquid comprises preferably either the same solvent contained in the first liquid or first reactant contained in the first liquid. For example, in the case of preparation of adipic acid from cyclohexane, the cooling liquid preferably comprises acetic acid (solvent), or cyclohexane (first reactant), or a mixture thereof. Preferably, no catalyst is contained in the cooling liquid. The temperature at which the cooling liquid is atomized is such that condensibles condense on the droplets of the atomized cooling liquid, and also on the curtain 1445, thus providing internal inside condensation. Since the catalyst (metal salt for example, such as cobalt acetate, for example) in most cases is not volatile, it does not transfer to the curtain 1445. Further, the temperature of the thick film is lower than that of the temperature of the first liquid droplets. Thus, no substantial reaction takes place within the curtain 1445, and in addition to other advantages, the thick film or curtain 1445 prevents solid buildup on the walls of the condenser. Liquids and droplets ar finally mixed together at the lower end 1416 of the reaction chamber 1412, as the second liquid 1454, which is removed through line 1424 for further treatment, as described in previous embodiments.

Many catalysts used for the oxidation are transition metals having more than one valence states. Their major catalytic action is exhibited when they are at a higher valance state than their lowest valance state at which they exist as ions. One good example is cobalt in the case of oxidation of cyclohexane to adipic acid. An initiation period before the oxidation starts has often been attributed by researches to the addition of cobalt ions at a valance state of II. The cobalt catalyst is added at valance state II because cobaltous acetate, for example, is more readily available and it is less expensive than cobaltic acetate. Thus, it takes a period of time for the cobaltous ion to be oxidized to cobaltic ion and start acting as a catalyst according to methods in the art so far, unless cobalt II is used, or the cobalt II is preoxidized. Even then, it takes time to oxidize cobalt II to cobalt III ions, due to the small interface provided by bubbling the gas through the solution.

In the case of the instant invention, this period of oxidation becomes considerably smaller because of the high surface area provided.

Figure 18:
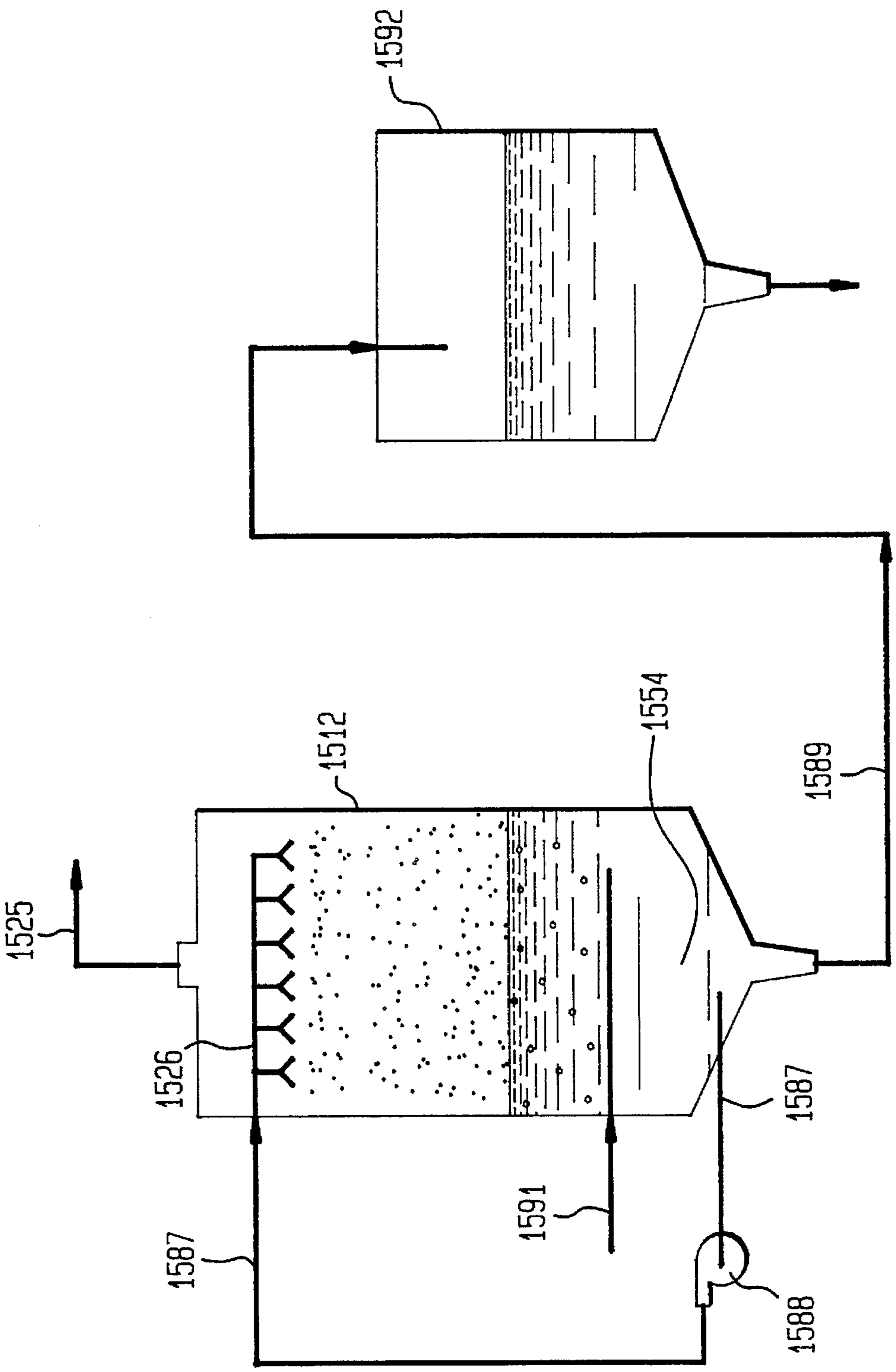
FIG. 18 illustrates schematically an apparatus for oxidizing metal ion catalysts according to this invention.

In addition, the cobaltous ion can be pre-oxidized using substantially the methods and devices of the instant invention. In this respect, the cobaltous ions, in the form of cobaltous acetate tetrahydrate for example are dissolved in water, acetic acid, or a mixture thereof, for example, to form a solution. In a reaction chamber 1 512, similar the aforedescribed reaction chambers, better shown in FIG. 18, the solution is broken to droplets by an atomizer 1526 in a stream of a gas containing a second reactant, preferably oxygen, for example. The gas enters the reaction chamber 1512 through line 1591 and leaves through exhaust line 1525. It is recirculated through line 1587 from the solution 1554 to the atomizer 1526 by means of a pump 1588. Cobalt II ions in the droplets are oxidized fast to cobalt III ions, due not only to the huge surface area, but also to the fact that the second reactant has only very small distances to travel within each droplet, in order to affect the total liquid. A sampling monitor (not shown) follows the progress of the oxidation. The sampling monitor may use any of the analytical techniques, well known to the art, for determining the progress of oxidation. When a substantial amount of Co (II) has been oxidized to Co (III), the solution 1554 is transferred to a retaining tank 1592, from which, it is added to any appropriate stage of the process. For example, in the case of the embodiment shown in FIG. 1, it may be added in the recirculation tank 19, or in line 41, or in line 42. For other catalyst systems comprising other than cobalt metal ions, the same process may be used, so as to cause at least partial oxidation of the lower valance state ions to ions of higher valance state in the solution of said metal catalyst.

As aforementioned, oxidations according to this invention, are non-destructive oxidations, wherein the oxidation product is different than carbon monoxide, carbon dioxide, and a mixture thereof. Of course, small amounts of these compounds may be formed along with the oxidation product, which may be one product or a mixture of products.

Examples include, but of course, are not limited to preparation of $C_5$–$C_8$ aliphatic dibasic acids from the corresponding saturated cycloaliphatic hydrocarbons, such as for example preparation of adipic acid from cyclohexane;

preparation of $C_5$–$C_8$ aliphatic dibasic acids from the corresponding ketones, alcohols, and hydroperoxides of saturated cycloaliphatic hydrocarbons, such as for example preparation of adipic acid from cyclohexanone, cyclohexanol, and cyclohexylhydroperoxide;

preparation of $C_5$–$C_8$ cyclic ketones, alcohols, and hydroperoxides from the corresponding saturated cycloaliphatic hydrocarbons, such as for example preparation of cyclohexanone, cyclohexanol, and cyclohexylhydroperoxide from cyclohexane; and preparation of aromatic multi-acids from the corresponding multi-alkyl aromatic compounds, such as for example preparation of phthalic acid, isophthalic acid, and terephthalic acid from o-xylene, m-xylene and p-xylene, respectively.

Regarding adipic acid, the preparation of which is especially suited to the methods and apparatuses of this invention, general information may be found in a plethora of U.S. Patents, among other references. These, include, but are not limited to:

U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); 4,263,453; 4,331,608; 4,606,863; 4,902,827; 5,221,800; and 5,321,157.

Examples demonstrating the operation of the instant invention have been given for illustration purposes only, and should not be construed as limiting the scope of this invention in any way. In addition it should be stressed that the preferred embodiments discussed in detail hereinabove, as well as any other embodiments encompassed within the limits of the instant invention, may be practiced individually, or in any combination thereof, according to common sense and/or expert opinion. Individual sections of the embodiments may also be practiced individually or in combination with other individual sections of embodiments or embodiments in their totality, according to the present invention. These combinations also lie within the realm of the present invention. Furthermore, any attempted explanations in the discussion are only speculative and are not intended to narrow the limits of this invention.

In the different figures of the drawing, numerals differing by 100 represent elements which are either substantially the same or perform the same function. Therefore, in the case that one element has been defined once in a certain embodiment, its re-definition in other embodiments illustrated in the figures by the same numerals or numerals differing by 100 is not necessary, and it has been often omitted in the above description for purposes of brevity.

The words "inlet line" and "outlet line" have been used to signify lines adapted to transfer materials for the operation of the process, such as volatiles, intermediate oxidation products, off-gases, and the like, for example. The words "input line" and "output line" have been used to signify lines adapted to transmit signals, which are mostly electrical, but they could also be hydraulic, pneumatic, optical, acoustic, and the like, for example.

A diagonal arrow through an element denotes that the element is controlled though a line, preferably electrical, connected to the arrow.

Internal condensation according to this invention is condensation of condensibles, which takes place within the pressurized system and before pressure drop to about atmospheric pressure.

Condensibles are substances having a boiling point higher than 15° C., while non condensibles are substances that have a boiling point of 15° C. and lower. It should be understood that when referring to condensibles, it is meant "mostly condensibles" and when referring to non-condensibles it is meant "mostly non-condensibles", since small amounts of one kind will be mixed with the other kind at substantially all times.

More specifically the transient conversion is defined as the ratio $$(O^2-O^1)\times 100/R^1\times n$$

where:

$O^1$ is the percent moles of intermediate oxidation product in the first liquid;

$O^2$ is the percent moles of intermediate oxidation product as provided to the conversion monitor by the sample collector;

$R^1$ is the percent moles of first reactant in the first liquid; and n is the number of moles of intermediate oxidation product produced when one mole of first reactant is completely converted to said intermediate oxidation product.

In other words, transient conversion is the conversion taking place in the time interval between the formation of the droplets and their coalescence into a mass of liquid.

In cases where dilution or concentration of the droplets occurs as they travel from the atomizer to the sample collector, such dilution has to be taken into acount in the calculation of transient conversion in the appropriately programmed controller by monitoring the sources of dilution or concentration using well known to the art techniques.

Response time between changing one variable or parameter and the result it brings about should also be taken into account, and the controller calibrated or programmed accordingly, by well known to the art techniques.

What is claimed is:

1. A method of preparing an intermediate oxidation product from a first liquid containing a first reactant and a gas containing an oxidant, the method comprising the steps of:

atomizing the first liquid to form a plurality of droplets in the gas at an atomization temperature and at an atomization distance from a mass of a second liquid;

causing a substantially non-destructive oxidation at an oxidation pressure between the first reactant and the oxidant to form the intermediate oxidation product;

coalescing the droplets into the mass of the second liquid; controlling transient conversion of the first reactant and the oxidant to intermediate oxidation product in the droplets to be within a predetermined pre-coalescing transient conversion range, before said droplets coalesce into the second liquid; and separating the intermediate oxidation product from the second liquid.

2. A method as defined in claim 1, wherein the droplets have an average droplet diameter and are produced at a desired first flow rate, the gas flows at a second flow rate, the droplets contain volatile ingredients volatilizing at a volatilization rate, the first liquid contains first reactant at a first content, the gas contains oxidant at a second content, and controlling of the transient conversion is performed by a step selected from a group consisting of changing the atomization temperature, changing the reaction pressure, changing the atomization distance, changing the average droplet diameter, changing the first flow rate, changing the second flow rate, changing the volatilization rate, changing the first content, changing the second content, and a combination thereof.

3. A method as defined in claim 2, wherein the transient conversion is monitored by a chromatographic method.

4. A method as defined in claim 2, wherein the transient conversion is monitored by High Performance Liquid Chromatography.

5. A method as defined in claim 1, wherein a major portion of the oxidation product is an organic compound.

6. A method as defined in claim 5, wherein the first reactant is an organic compound.

7. A method as defined in claim 6, wherein the oxidant is oxygen.

8. A method as defined in claim 7, wherein the major portion of the oxidation product is an intermediate oxidation product different than CO, $CO_2$ or a mixture thereof.

9. A method as defined in claim 8, wherein the major portion of the intermediate oxidation product is an organic acid.

10. A method as defined in claim 9, wherein the organic acid is adipic acid.

11. A method as defined in claim 10, wherein the predetermined transient conversion range is 5% to 80%.

12. A method as defined in claim 9, wherein the organic acid is terephthalic acid.

13. A method as defined in claim 12, wherein the predetermined transient conversion range is 5% to 80%.

14. A method as defined in claim 8, wherein the first reactant comprises a compound selected from a group consisting of cyclohexane, cyclohexanone, cyclohexanol, cyclohexylhydroperoxide, o-xylene, p-xylene, m-xylene, a mixture of at least two of cyclohexane, cyclohexanone, cyclohexanol, and cyclohexylhydroperoxide, and a mixture of at least two of o-xylene, p-xylene, and m-xylene.

15. A method as defined in claim 14, wherein the first reactant comprises a compound selected from a group consisting of cyclohexane, cyclohexanone, cyclohexanol, and a mixture thereof.

16. A method as defined in claim 8, wherein the first reactant comprises cyclohexane.

17. A method as defined in claim 8, wherein the first reactant comprises cyclohexanone.

18. A method as defined in claim 14, wherein the first reactant comprises a compound selected from a group consisting of o-xylene, p-xylene, m-xylene and a mixture thereof.

19. A method as defined in claim 8, wherein the first reactant comprises p-xylene.

20. A method as defined in claim 3, wherein the first reactant comprises a compound selected from a group consisting of cyclohexane, cyclohexanone, cyclohexylhydroxyperoxide, cyclohexanol, o-xylene, m-xylene, p-xylene, a mixture of at least two of cyclohexane, cyclohexanone, cyclohexanol, and cyclohexylhydroxyperoxide, and a mixture of at least two of o-xylene, p-xylene, and m-xylene;

the oxidant comprises oxygen; and a major portion of the reaction product comprises a compound selected from a group consisting of adipic acid, cyclohexanol, cyclohexanone, cyclohexylhydroperoxide, phthalic acid, isophthalic acid, terephthalic, a mixture of at least two of adipic acid, cyclohexanone, cyclohexanol, and cyclohexylhydroxyperoxide, and a mixture of at least two of phthalic acid, isophthalic acid, and terephthalic acid.

21. A method as defined in claim 1, wherein the step of atomizing is performed by spraying the first liquid from a point over the second liquid at the atomization distance.

22. A method as defined in claim 21, wherein spraying is performed by an airless technique.

23. A method as defined in claim 1, wherein at least part of the second liquid is recirculated.

24. A method as defined in claim 23, wherein a third liquid containing first reactant is also added to the first liquid to replenish first reactant consumed during the substantially non-destructive oxidation.

25. A method as defined in claim 24, wherein the intermediate oxidation product is a solid, and the step of separating said intermediate oxidation product from the second liquid includes a step of filtering the intermediate oxidation product out of the second liquid.

26. A method as defined in claim 1, wherein an adequate amount of antistatic compound is added to a component selected from a group consisting of the first liquid, the gas, and a combination thereof, in order to prevent development of electrostatic charges and sparking.

27. A method as defined in claim 26, wherein the antistatic compound comprises water.

28. A method as defined in claim 1, further comprising a step of internally condensing condensibles substantially under reaction pressure.

29. A method as defined in claim 1, wherein the non-destructive oxidation is conducted in a reaction zone surrounded by a thick film or curtain of liquid.

30. A method as defined in claim 14, wherein the non-destructive oxidation is conducted in a reaction zone surrounded by a thick film or curtain of liquid.

31. A method as defined in claim 1, further comprising a step of adding a catalyst to the first liquid, the catalyst comprising metal ions, the ions being able to exist at a state selected from a group consisting of a lower valance state, a higher valance state, and a mixture thereof, the catalyst having been formed by steps of atomizing a solution comprising metal ions of the lower valance state to form a plurality of droplets in a gas containing an oxidant;

causing at least partial oxidation of the lower valance state ions to ions of higher valance state in the solution.

32. A method as defined in claim 14, further comprising a step of adding a catalyst to the first liquid, the catalyst having been formed by steps of atomizing a solution comprising bivalent cobalt ions to form a plurality of droplets in a gas containing an oxidant;

causing at least partial oxidation of the bivalent cobalt ion to trivalent cobalt ion.

33. A method as defined in claim 2, wherein control of transient conversion is performed by changing the catalyst level in the first liquid.

* * * * *